(12) United States Patent
Koziel et al.

(10) Patent No.: US 7,989,679 B2
(45) Date of Patent: *Aug. 2, 2011

(54) METHODS AND COMPOSITIONS FOR IMPROVED ENZYME ACTIVITY IN TRANSGENIC PLANTS

(75) Inventors: Michael G. Koziel, Raleigh, NC (US); Laura Cooper Schouten, Pittsboro, NC (US); Brian Vande Berg, Durham, NC (US)

(73) Assignee: Athenix Corp., Morrisville, NC (US)

( * ) Notice: Subject to any disclaimer, the term of this patent is extended or adjusted under 35 U.S.C. 154(b) by 352 days.

This patent is subject to a terminal disclaimer.

(21) Appl. No.: 11/681,285

(22) Filed: Mar. 2, 2007

(65) Prior Publication Data

US 2007/0289031 A1    Dec. 13, 2007

Related U.S. Application Data

(60) Provisional application No. 60/778,283, filed on Mar. 2, 2006, provisional application No. 60/891,977, filed on Feb. 28, 2007.

(51) Int. Cl.
C12N 15/82 (2006.01)
(52) U.S. Cl. .................. 800/300; 800/268; 800/298
(58) Field of Classification Search .......... None
See application file for complete search history.

(56) References Cited

U.S. PATENT DOCUMENTS

| | | | |
|---|---|---|---|
| 4,535,060 A | 8/1985 | Comai | |
| 4,710,461 A | 12/1987 | Komano et al. | |
| 4,761,373 A | 8/1988 | Anderson et al. | |
| 4,769,061 A | 9/1988 | Comai | |
| 4,810,648 A | 3/1989 | Stalker | |
| 4,940,835 A | 7/1990 | Shah et al. | |
| 4,971,908 A | 11/1990 | Kishore et al. | |
| 4,975,374 A | 12/1990 | Goodman | |
| 5,013,659 A | 5/1991 | Bedbrook | |
| 5,094,945 A | 3/1992 | Comai | |
| 5,141,870 A | 8/1992 | Bedbrook | |
| 5,145,783 A | 9/1992 | Kishore | |
| 5,188,642 A | 2/1993 | Shah | |
| 5,198,599 A | 3/1993 | Thill | |
| 5,304,732 A | 4/1994 | Anderson | |
| 5,310,667 A | 5/1994 | Eichholtz | |
| 5,312,910 A | 5/1994 | Kishore | |
| 5,331,107 A | 7/1994 | Anderson | |
| 5,378,824 A | 1/1995 | Bedbrook | |
| 5,380,831 A | 1/1995 | Adang | |
| 5,391,725 A | 2/1995 | Coruzzi | |
| 5,463,175 A | 10/1995 | Barry | |
| 5,489,520 A | 2/1996 | Adams | |
| 5,491,288 A | 2/1996 | Chaubet | |
| 5,510,471 A | 4/1996 | Lebrun | |
| 5,550,318 A | 8/1996 | Adams | |
| 5,561,236 A | 10/1996 | Leemans | |
| 5,605,011 A | 2/1997 | Bedbrook | |
| 5,627,061 A * | 5/1997 | Barry et al. ............ 800/288 |
| 5,633,435 A | 5/1997 | Barry | |
| 5,633,448 A | 5/1997 | Lebrun | |
| 5,646,024 A | 7/1997 | Leemans | |
| 5,648,477 A | 7/1997 | Leemans | |
| 5,731,180 A | 3/1998 | Dietrich | |
| 5,767,361 A | 6/1998 | Dietrich | |
| 5,767,373 A | 6/1998 | Ward | |
| 5,776,760 A | 7/1998 | Barry | |
| 5,804,425 A | 9/1998 | Barry | |
| 5,866,775 A | 2/1999 | Eichholtz | |
| 5,874,265 A | 2/1999 | Adams | |
| 5,879,903 A | 3/1999 | Strauch | |
| 5,919,675 A | 7/1999 | Adams | |
| 5,928,937 A | 7/1999 | Kakefuda | |
| 5,969,213 A | 10/1999 | Adams | |
| RE36,449 E | 12/1999 | Lebrun | |
| 6,040,497 A | 3/2000 | Spencer | |
| 6,084,155 A | 7/2000 | Volrath | |
| 6,130,366 A | 10/2000 | Herrera-Estrella | |
| 6,177,616 B1 | 1/2001 | Bartsch | |
| 6,225,114 B1 | 5/2001 | Eichholtz | |
| 6,248,876 B1 | 6/2001 | Barry | |
| RE37,287 E | 7/2001 | Lebrun | |
| 6,282,837 B1 | 9/2001 | Ward | |
| 6,288,306 B1 | 9/2001 | Ward | |

(Continued)

FOREIGN PATENT DOCUMENTS

EP    0333033 A1    9/1989

(Continued)

OTHER PUBLICATIONS

Burke et al., "A selection procedure for indentifying transgenic cells and embryos of cotton withouth the use of antibiotics," (2008) *in Vitro Cell. Dev. Biol. Plant* 44:246-253.

Chatfield et al., "Complete nucleotide sequence of the aroA gene from *Salmonella typhi* encoding 5-enolpyruvylshikimate 3-phosphate synthase," (1990) *Nucleic Acids Res.* 18(20):6133.

Clark et al., "Mutations at the transit peptide-mature protein junction separate two cleavage events during chloroplast import of the chlorophyll a/b-binding protein." (1989) *J. Biol. Chem.*, 15;264(29):17544-17550.

Datta et al., "Herbicide-resistant Indica rice plants from IRRI breeding line IR72 after PEG-mediated transformation of protoplasts" (1992) *Plant Molecular Biology*, 20:619-629 (abstract only).

(Continued)

*Primary Examiner* — David H Kruse
(74) *Attorney, Agent, or Firm* — Destiny M. Davenport

(57) ABSTRACT

Compositions and methods for increasing enzyme activity across a broad physiological spectrum in plants, plant cells, tissues and seeds are provided. Compositions include plants or plant parts comprising two or more polynucleotides encoding polypeptides that are active across a broader physiological spectrum than when either polynucleotide is expressed alone. Vectors comprising these polynucleotide molecules as well as host cells comprising the vectors are further provided. Compositions also comprise transformed bacteria, plants, plant cells, tissues, and seeds. In addition, methods are provided for producing the plants, plant cells, tissues and seeds of the invention. Methods for increasing plant yield and methods for conferring resistance to an herbicide in a plant are further provided.

28 Claims, 4 Drawing Sheets

U.S. PATENT DOCUMENTS

| | | | |
|---|---|---|---|
| 6,338,961 B1 | 1/2002 | Derose | |
| 6,385,546 B1 | 5/2002 | Kahn | |
| 6,462,258 B1 * | 10/2002 | Fincher et al. | 800/300 |
| 6,566,587 B1 | 5/2003 | Lebrun | |
| 6,642,053 B1 | 11/2003 | Daniell | |
| 6,716,474 B2 | 4/2004 | Barry | |
| 6,727,084 B1 | 4/2004 | Hoyoux et al. | |
| 6,781,034 B2 | 8/2004 | Palatnik | |
| 6,902,915 B2 | 6/2005 | Tokuyama | |
| 7,026,527 B2 | 4/2006 | Falco | |
| 7,071,383 B2 | 7/2006 | Falco | |
| 7,674,958 B2 * | 3/2010 | Peters et al. | 800/300 |
| 2002/0112260 A1 | 8/2002 | Schillinger | |
| 2004/0082770 A1 | 4/2004 | Castle | |
| 2004/0177399 A1 | 9/2004 | Hammer | |
| 2005/0223436 A1 | 10/2005 | Lin. | |
| 2005/0246798 A1 * | 11/2005 | Castle et al. | 800/300 |
| 2006/0150270 A1 | 7/2006 | Hammer | |
| 2007/0136840 A1 | 6/2007 | Peters | |
| 2007/0169218 A1 | 7/2007 | Carr | |

FOREIGN PATENT DOCUMENTS

| | | |
|---|---|---|
| EP | 0242246 B1 | 11/1992 |
| EP | 0242236 B2 | 8/1996 |
| EP | 1173582 B1 | 6/2006 |
| WO | WO 96/33270 | 10/1996 |
| WO | WO 00/66746 | 11/2000 |
| WO | WO 00/66747 | 11/2000 |
| WO | WO 01/12825 | 2/2001 |
| WO | WO 01/66704 | 9/2001 |
| WO | WO/08105905 | 9/2008 |

OTHER PUBLICATIONS

De Greef et al., "Evaluation of Herbicide Resistance in Transgenic Crops Under Field Conditions," (1989) *BioTechnology* 7(1): 61-64.
Della-Cioppa et al., "Protein trafficking in plant cells," (1987) *Plant Physiol.*, 84:965-968.
Della-Cioppa et al., "Translocation of the precursor of 5-enolpyruvylshikimate-3-phosphate synthase into chloroplasts of higher plants in vitr,"(1986) *Proc.Natl. Acad. Sci. U.S.A*, 83: 6873-6877.
Du et al., "Characterization of *Streptococcus pneumoniae* 5-enolpyruvylshikimate 3-phosphate synthase and its activation by univalent cations," (2000) *Eur. J. Biochem.*, 267(1):222-227.
Duncan et al., "The complete amino acid sequence of *Escherichia coli* S-enolpyruvylshikimate 3-phosphate synthase," (1984) *FEBS Letters.*, 170:59-63.
Eschenburg et al., "How the mutation glycine96 to alanine confers glyphosate insensitivity to 5-enolpyruvyl shikimate-3-phosphate synthase from *Escherichia coli*," (2002) *Planta*, 216(1):129-135.
Gaynor et al., "Subceliular Localization of Rice Leaf Aryl Acylamidase Activity,"(1983) *Plant Physiol.*, 72: 80-85.

Hayes et al., "Molecular cloning and heterologous expression of a cDNA encoding a mouse glutathione S-transferase Yc subunit possessing high catalytic activity for aflatoxin B1-8,9-epoxide," (1992) *Biochem. J.*, 285:173-180.
He et al., "A T42M substitution in bacterial 5-enolpyruvylshikimate-3-phosphate synthase (EPSPS) generates enzymes with increased resistance to glyphosate," (2003) *Biosci. Biotechnol. Biochem.*, 67(6):1405-1409.
Horsburgh et al., "Chorismate synthase from *Staphylococcus aureus*," (1996) *Microbiology*, 142(Part 10):2943-2950.
Kishore et al., "Amino acid biosynthesis inhibitors as herbicides," (1988) *Ann. Rev. Biochem.* 57:627-663.
Lee et al., "The molecular basis of sulfonylurea herbicide resistance in tobacco," (1988) *EMBO Journal* 7(5):1241-1248.
Light et al., "A thermal application range for postemergence pyrithiobac applications," (2001) *Weed Science*, 49:543-548.
Light et al., "Thermal dependence of pyrithiobac efficacy in *Amaranthus palmeri*," (1999) *Weed Science*, 47(6):644-650.
Oliver et al., "Inhibition of tobacco NADH-hydroxypyruvate reductase by expression of a heterologous antisense RNA derived from a cucumber c DNA: Implications fro the mechanism of action of antisense RNAs," (1993) *Mol. Gen. Genet.*, 239:425-434.
Przibilla et al., "Site-Specific mutagenesis of the D1 Subunit of Photosystem II in Wild-Type Chlamydomonas," (1991) *Plant Cell*, 3:169-174.
Reinbothe et al., "Overproduction by gene amplification of the multifunctional arm protein confers glyphosate tolerance to a plastid-free mutant of *Euglena gracilis*," (1993) *Mol. Gen. Genet.*, 239:421-424.
Selvapandiyan et al., Point mutation of a conserved arginine (104) to lysine introduces hypersensitivity to inhibition by glyphosate in the 5-enolpyruvylshikimate-3-phosphate synthase of *Bacillus subtilis*, (1995) *Letters* 374(2):253-256.
Schonbrunn et al., "Interaction of the herbicide glyphosate with its target enzyme 5-enolpyruvylshikimate 3-phosphate synthase in atomic detail,"(2001) *Proc. Natil. Acad. Sci. U.S.A.*, 98:1376-1380.
Shiota et al., "Herbicide-resistant tobacco plants expressing the fused enzyme between rat cytochrome P4501A1 (CYP1A1) and yeast NADPH-cytochrome P450 oxidoreductase," (1994) *Plant Physiol.*, 106:17-23.
Shuttleworth et al., "Site-directed mutagenesis of putative active site residues of 5-enolpyruvylshikimate-3-phosphate synthase," (1999) *Biochemistry*, 38(1):296-302.
Wang et al., "Plant responses to drought, salinity and extreme temperatures: towards genetic engineering for stress tolerance," (2003) *Planta*, 218:1-14.
Wu et al., "Stromel pH and Photosynthesis Are Affected by Electroneutral K+ and H+ Enchange through Chloroplast Envelope Ion Channels" (1992) *Plant Physiol*. 98:666-672.

* cited by examiner

SEQUENCE LISTING

```
<160> NUMBER OF SEQ ID NOS: 8

<210> SEQ ID NO 1
<211> LENGTH: 2000
<212> TYPE: DNA
<213> ORGANISM: Brevundimonas vesicularis
<220> FEATURE:
<221> NAME/KEY: CODING_REGION
<222> LOCATION: (296)..(1555)

<400> SEQUENCE: 1
ggtttcgtcg aattgcagca gtcgctggag cggaccgaaa acgaaatcca gatgtcgcgc      60
cgctattaca acggtgccgc acgcgatctg aacgtcaagg tcgagacctt cccgaacaat     120
ctcattgccg gccccttcgg cttcgtcaag aaggcctatt tcgagatcac caacgaggcc     180
gatcgcgccg ttcccacggt caagttctaa gattttcgct atcggttttt catgcaaggc     240
ggtaaaggat ggccgaccgc cggccatcgg ccgtttcct gactgaccaa agagaatgat     300
gatgggtaga gccaaactca cgattatccc gccgggcaag cctttgaccg gacgcgccat     360
gccgccggga tcgaagtcga tcaccaaccg cgcattgctg ctcgccggcc tcgccaaggg     420
cacgagccgg ctaaccggtg cgctgaagag cgacgatacc cgctatatgg ccgaagcgct     480
gcgtgcgatg ggtgtaacga tcgacgagcc cgacgacacc acgttcatcg tcaaaggcag     540
cggcaagctg cagccgccgg cagccccgct tttcctcggc aatgccggca cggcaacgcg     600
cttcctgacg gcggccgcgg cactggtgga cggcaaggtc atcgtcgacg gcgatgccca     660
tatgcgcaag cggccgatcg gaccgctagt cgacgcgttg cgctcgctcg gcatcgatgc     720
```

```
ctcggctgaa accggctgcc cgccagtcac gatcaacggc accggccgct tcgaggcaag      780
ccgcgtgcag atcgatggcg gcctgtccag ccagtatgtc tcggcgctcc tgatgatggc      840
cgccggcggc gatcgcgctg tcgatgtcga gcttctcggc gaacatatcg gcgctctcgg      900
ctatatcgac ctgaccgttg ccgccatgcg cgctttcggc gcgaaggttg agcgtgtgag      960
cccggtcgcc tggcgcgtcg agcccaccgg ctatcatgcg gccgacttcg tgatcgagcc     1020
ggatgcctct gctgcgacct atctctgggc cgccgaagtt ctgagcggcg caagatcga      1080 tctcggcacg ccggcggaac agttctcgca accggatgcg aaagcctatg atctgatttc     1140
gaaattcccg catctgcctg ctgtcatcga cggctcgcag atgcaggacg ccatcccgac     1200
gctcgccgtt ctcgccgctt caacgaaat gcctgtgcgc ttcgtcggta tcgaaaacct      1260
gcgcgtcaag gaatgcgatc gtatccgcgc gctctcgagc ggcctatccc gcatcgttcc     1320
gaacctcggc acggaagagg gcgacgatct catcatcgcc tccgatccga gccttgccgg     1380
caaaatcctg accgcagaga tcgatagctt tgccgatcac cgcatcgcca tgagctttgc     1440
gctggccggc ctgaagatcg gcggcattac cattctcgac cccgactgcg tcgccaagac     1500
attcccgtcc tactgaatg tgctgtcttc gctgggggtc gcctacgaag actgacgctc      1560
tgctcctata gaggcctgag cgcggattta ttcttgacgc aaagcggcgc cggtaacggc     1620
gccgcaggca tcttttgggg gaatgatgac acggctctgc gggttttttgc tggccttgtg    1680 cctgatgctt tgtgcaacgg cggtgacggc cgccgagctc atcagcaatt ttgatcaggc     1740
aattgcgttg catcgtgatg gctccatgcg ggtcgtcgaa acgatttccg tcaatgccga     1800
ggggcgcgat atccgccgcg gcatcttccg cgatttcccg ctgaccttca tcgatgcgaa     1860
aggccgtgaa agcgaggttg attttgcggt cgtctccgtc gagcgcgacg gcgagccgga     1920
agaatggcgt atcgaacgca tcaaaggcgg tgagcgcatc tatatcggca atgcgcaaac     1980
atttctggat agcggtcctc                                                 2000
```

<210> SEQ ID NO 2
<211> LENGTH: 419
<212> TYPE: PRT
<213> ORGANISM: Brevundimonas vesicularis

<400> SEQUENCE: 2

```
Met Met Met Gly Arg Ala Lys Leu Thr Ile Ile Pro Pro Gly Lys Pro
1               5                   10                  15

Leu Thr Gly Arg Ala Met Pro Pro Gly Ser Lys Ser Ile Thr Asn Arg
            20                  25                  30

Ala Leu Leu Leu Ala Gly Leu Ala Lys Gly Thr Ser Arg Leu Thr Gly
        35                  40                  45

Ala Leu Lys Ser Asp Asp Thr Arg Tyr Met Ala Glu Ala Leu Arg Ala
    50                  55                  60

Met Gly Val Thr Ile Asp Glu Pro Asp Thr Phe Ile Val Lys
65                  70                  75                  80

Gly Ser Gly Lys Leu Gln Pro Pro Ala Ala Pro Leu Phe Leu Gly Asn
                85                  90                  95

Ala Gly Thr Ala Thr Arg Phe Leu Thr Ala Ala Ala Leu Val Asp
            100                 105                 110

Gly Lys Val Ile Val Asp Gly Asp Ala His Met Arg Lys Arg Pro Ile
        115                 120                 125

Gly Pro Leu Val Asp Ala Leu Arg Ser Leu Gly Ile Asp Ala Ser Ala
    130                 135                 140
```

```
Glu Thr Gly Cys Pro Pro Val Thr Ile Asn Gly Thr Gly Arg Phe Glu
145                 150                 155                 160

Ala Ser Arg Val Gln Ile Asp Gly Gly Leu Ser Gln Tyr Val Ser
            165                 170                 175

Ala Leu Leu Met Met Ala Ala Gly Gly Asp Arg Ala Val Asp Val Glu
            180                 185                 190

Leu Leu Gly Glu His Ile Gly Ala Leu Gly Tyr Ile Asp Leu Thr Val
            195                 200                 205

Ala Ala Met Arg Ala Phe Gly Ala Lys Val Glu Arg Val Ser Pro Val
210                 215                 220

Ala Trp Arg Val Glu Pro Thr Gly Tyr His Ala Ala Asp Phe Val Ile
225                 230                 235                 240

Glu Pro Asp Ala Ser Ala Ala Thr Tyr Leu Trp Ala Ala Glu Val Leu
                245                 250                 255

Ser Gly Gly Lys Ile Asp Leu Gly Thr Pro Ala Glu Gln Phe Ser Gln
            260                 265                 270

Pro Asp Ala Lys Ala Tyr Asp Leu Ile Ser Lys Phe Pro His Leu Pro
        275                 280                 285

Ala Val Ile Asp Gly Ser Gln Met Gln Asp Ala Ile Pro Thr Leu Ala
        290                 295                 300

Val Leu Ala Ala Phe Asn Glu Met Pro Val Arg Phe Val Gly Ile Glu
305                 310                 315                 320

Asn Leu Arg Val Lys Glu Cys Asp Arg Ile Arg Ala Leu Ser Ser Gly
                325                 330                 335

Leu Ser Arg Ile Val Pro Asn Leu Gly Thr Glu Glu Gly Asp Asp Leu
            340                 345                 350

Ile Ile Ala Ser Asp Pro Ser Leu Ala Gly Lys Ile Leu Thr Ala Glu
            355                 360                 365

Ile Asp Ser Phe Ala Asp His Arg Ile Ala Met Ser Phe Ala Leu Ala
        370                 375                 380

Gly Leu Lys Ile Gly Gly Ile Thr Ile Leu Asp Pro Asp Cys Val Ala
385                 390                 395                 400

Lys Thr Phe Pro Ser Tyr Trp Asn Val Leu Ser Ser Leu Gly Val Ala
                405                 410                 415

Tyr Glu Asp

<210> SEQ ID NO 3
<211> LENGTH: 1892
<212> TYPE: DNA
<213> ORGANISM: Arthrobacter globiformis
<220> FEATURE:
<221> NAME/KEY: CODING_REGION
<222> LOCATION: (109)..(1416)
<223> OTHER INFORMATION: Strain ATX21308
<220> FEATURE:
<221> NAME/KEY: misc_feature
<222> LOCATION: (1801)..(1801)
<223> OTHER INFORMATION: n = a, c, g, or t

<400> SEQUENCE: 3
gggaccacat gctgctcctg atttcagggc tgctgccggt atggaccagg gtttagagag      60
ggacggcacg catccgggcc cttatcggac caacgccaac agcggtcggt ggccttggag     120
cggggccagc acgccgatc acgtagactc tttggagctt cgctcgaaag gatcaccatg     180
gaaactgatc gactagtgat cccaggatcg aaaagcatca ccaaccgggc tttgcttttg     240
gctgccgcag cgaagggcac gtcggtcctg gtgagaccat tggtcagcgc cgatacctca     300
gcattcaaaa ctgcaattca ggccctcggt gccaacgtct cagccgacgg tgacaattgg     360
```

```
gtcgttgaag gcctgggtca ggcaccccac ctcgacgccg acatctggtg cgaggatgca     420
ggtaccgtgg cccggttcct ccctccattc gtcgccgcag acaggggaa gttcaccgtc       480 gacggaagcg agcagctgcg gcggcgcccg cttcggcccc tggtcgacgg catccgccac     540
ctgggcgccc gcgtctcctc cgagcagctg cccctaacaa ttgaagcgag cgggctggca     600
ggcggggagt acgaaattga agcccatcag agcagccagt cgcctccgg cctgatcatg      660 gccgccccgt acgcgcgaca aggcctgcgt gtgcggatac caaatcccgt gagccagccc     720
tacctcacga tgacactgcg gatgatgagg gacttcggcc ttgagaccag caccgacgga    780
gccaccgtca gcgtccctcc cgggcgctac acagcccggc ggtatgaaat tgaaccggac    840
gcgtcaactg cgtcgtactt cgccgccgct tccgccgtct ctggccgaag cttcgaattc     900
cagggccttg gcacagacag catccaaggc gacacgtcat tcttcaatgt acttgggcgg   960
ctcggtgcag aggtccactg gcacccaac tcggtcacca tatccggacc ggaaaggctg     1020
aacggcgaca ttgaagtgga tatgggcgag atatcggaca ccttcatgac actcgcggcg    1080 attgccccctc tagccgatgg acccatcacg ataaccaaca ttggccatgc acggttgaag    1140
gaatccgacc gcatctcggc gatggaaacc aacctgcgaa cgctcggtgt acaaaccgac    1200
gtcggacacg actggatgcg aatctacccc tctaccccgc acggcggcag agtcaattgc    1260
caccgggacc acaggatcgc catggcgttt caatcctgg gactgcgagt ggacgggatt     1320
accctcgacg accctcaatg tgtcgggaag acctttcctg gcttcttcga ctaccttgga    1380
cgccttttcc ccgaaaaggc gcttacgctc cccggctagt gacttcctct ccggcggacg    1440
ctaggcatcg gaaaacgaat cctgacatga ccgacctcct cgcgtcacgg cgtgtctgcc    1500
ggtacccaag cattctgcct tagccgcttc cgcggccccct tatgctttct ggttgtccag   1560
attttcatcc gggatgttgc ctgaccttga gcagggcaat cagctgttca gcactgtcaa    1620
tggtgtgggc cctgaaggcg gcttcgatgg ctgccacgtc ggcggctctc atcgctgtca    1680
cgacacgcag atgcgcttca taggcacgtt caggatccgc cctcgtcgcc tgatcctgag    1740
ccaaggcaat agttagatgt gcctccgttg gcggccagag ccgaagcaat aaggagtttt   1800
ncgaggccac ccagattccc cgggtggaag gcgatatggg cttcatgctg aactatgggg   1860
tccggatgga agtgactttt caactctgcc ca                                    1892
```

<210> SEQ ID NO 4
<211> LENGTH: 436
<212> TYPE: PRT
<213> ORGANISM: Arthrobacter globiformis
<220> FEATURE:
<221> NAME/KEY: VARIANT
<222> LOCATION: (1)..(436)
<223> OTHER INFORMATION: Strain ATX21308

<400> SEQUENCE: 4

Met Ala Leu Glu Arg Gly Gln His Gly Arg Ser Arg Arg Leu Phe Gly
1               5                   10                  15

Ala Ser Leu Glu Arg Ile Thr Met Glu Thr Asp Arg Leu Val Ile Pro
            20                  25                  30

Gly Ser Lys Ser Ile Thr Asn Arg Ala Leu Leu Leu Ala Ala Ala Ala
        35                  40                  45

Lys Gly Thr Ser Val Leu Val Arg Pro Leu Val Ser Ala Asp Thr Ser
    50                  55                  60

Ala Phe Lys Thr Ala Ile Gln Ala Leu Gly Ala Asn Val Ser Ala Asp
65                  70                  75                  80

```
Gly Asp Asn Trp Val Glu Gly Leu Gly Gln Ala Pro His Leu Asp
                85                  90                  95

Ala Asp Ile Trp Cys Glu Asp Ala Gly Thr Val Ala Arg Phe Leu Pro
            100                 105                 110

Pro Phe Val Ala Ala Gly Gln Gly Lys Phe Thr Val Asp Gly Ser Glu
        115                 120                 125

Gln Leu Arg Arg Arg Pro Leu Arg Pro Leu Val Asp Gly Ile Arg His
    130                 135                 140

Leu Gly Ala Arg Val Ser Ser Glu Gln Leu Pro Leu Thr Ile Glu Ala
145                 150                 155                 160

Ser Gly Leu Ala Gly Gly Glu Tyr Glu Ile Glu Ala His Gln Ser Ser
                165                 170                 175

Gln Phe Ala Ser Gly Leu Ile Met Ala Ala Pro Tyr Ala Arg Gln Gly
            180                 185                 190

Leu Arg Val Arg Ile Pro Asn Pro Val Ser Gln Pro Tyr Leu Thr Met
        195                 200                 205

Thr Leu Arg Met Met Arg Asp Phe Gly Leu Glu Thr Ser Thr Asp Gly
    210                 215                 220

Ala Thr Val Ser Val Pro Pro Gly Arg Tyr Thr Ala Arg Arg Tyr Glu
225                 230                 235                 240

Ile Glu Pro Asp Ala Ser Thr Ala Ser Tyr Phe Ala Ala Ala Ser Ala
                245                 250                 255

Val Ser Gly Arg Ser Phe Glu Phe Gln Gly Leu Gly Thr Asp Ser Ile
            260                 265                 270

Gln Gly Asp Thr Ser Phe Phe Asn Val Leu Gly Arg Leu Gly Ala Glu
        275                 280                 285

Val His Trp Ala Pro Asn Ser Val Thr Ile Ser Gly Pro Glu Arg Leu
    290                 295                 300

Asn Gly Asp Ile Glu Val Asp Met Gly Glu Ile Ser Asp Thr Phe Met
305                 310                 315                 320

Thr Leu Ala Ala Ile Ala Pro Leu Ala Asp Gly Pro Ile Thr Ile Thr
                325                 330                 335

Asn Ile Gly His Ala Arg Leu Lys Glu Ser Asp Arg Ile Ser Ala Met
            340                 345                 350

Glu Thr Asn Leu Arg Thr Leu Gly Val Gln Thr Asp Val Gly His Asp
        355                 360                 365

Trp Met Arg Ile Tyr Pro Ser Thr Pro His Gly Gly Arg Val Asn Cys
    370                 375                 380

His Arg Asp His Arg Ile Ala Met Ala Phe Ser Ile Leu Gly Leu Arg
385                 390                 395                 400

Val Asp Gly Ile Thr Leu Asp Asp Pro Gln Cys Val Gly Lys Thr Phe
                405                 410                 415

Pro Gly Phe Phe Asp Tyr Leu Gly Arg Leu Phe Pro Glu Lys Ala Leu
            420                 425                 430

Thr Leu Pro Gly
        435

<210> SEQ ID NO 5
<211> LENGTH: 1398
<212> TYPE: DNA
<213> ORGANISM: Enterobacter sp.
<220> FEATURE:
<221> NAME/KEY: CODING_REGION
<222> LOCATION: (103)..(1398)

<400> SEQUENCE: 5
```

-continued

| | |
|---|---|
| aaaaaaggaa atgaactatg tgttgctgga aaaagtaggg aagggagtgg tgaagagtat | 60 |
| tccactggtt caattagaaa aaatcattca aggattacca aagtgaaagt aacaatacag | 120 |
| cccggagatc tgactggaat tatccagtca cccgcttcaa aaagttcgat gcagcgagct | 180 |
| tgtgctgctg cactggttgc aaaaggaata agtgagatca ttaatcccgg tcatagcaat | 240 |
| gatgataaag ctgccaggga tattgtaagc cggcttggtg ccaggcttga agatcagcct | 300 |
| gatggttctt tgcagataac aagtgaaggc gtaaaacctg tcgctccttt tattgactgc | 360 |
| ggtgaatctg gtttaagtat ccggatgttt actccgattg ttgcgttgag taaagaagag | 420 |
| gtgacgatca aagatctgg aagccttgtt acaagaccaa tggatttctt tgatgaaatt | 480 |
| cttccgcatc tcggtgtaaa agttaaatct aaccagggta aattgcctct cgttatacag | 540 |
| gggccattga aaccagcaga cgttacggtt gatgggtcct taagctctca gttccttaca | 600 |
| ggtttgttgc ttgcatatgc ggccgcagat gcaagcgatg ttgcgataaa agtaacgaat | 660 |
| ctcaaaagcc gtccgtatat cgatcttaca ctggatgtga tgaagcggtt tggtttgaag | 720 |
| actcccgaga atcgaaacta tgaagagttt tatttcaaag ccgggaatgt atatgatgaa | 780 |
| acgaaaatgc aacgatacac cgtagaaggc gactggagcg tggtgctttt tttactggta | 840 |
| gcgggggcta ttgccgggcc gatcacggta agaggtttgg atatagcttc gacgcaggct | 900 |
| gataaagcga tcgttcaggc tttgatgagt gcgaacgcag gtattgcgat tgatgcaaaa | 960 |
| gagatcaaac ttcatcctgc tgatctcaat gcatttgaat ttgatgctac tgattgcccg | 1020 |
| gatcttttc cgccattggt tgctttggcg tcttattgca aaggagaaac aaagatcaaa | 1080 |
| ggcgtaagca ggctggcgca taagaaagt gacagaggat tgacgctgca ggacgagttc | 1140 |
| gggaaaatgg gtgttgaaat ccaccttgag ggagatctga tgcgcgtgat cggagggaaa | 1200 |
| ggcgtaaaag gagctgaagt tagttcaagg cacgatcatc gcattgcgat ggcttgcgcg | 1260 |
| gtggctgctt taaaagctgt gggtgaaaca accatcgaac atgcagaagc ggtgaataaa | 1320 |
| tcctacccgg atttttacag cgatcttaaa caacttggcg gtgttgtatc tttaaaccat | 1380 |
| caatttaatt tctcatga | 1398 |

<210> SEQ ID NO 6
<211> LENGTH: 431
<212> TYPE: PRT
<213> ORGANISM: Enterobacter sp.

<400> SEQUENCE: 6

Met Lys Val Thr Ile Gln Pro Gly Asp Leu Thr Gly Ile Leu Gln Ser
1               5                   10                  15

Pro Ala Ser Lys Ser Ser Met Gln Arg Ala Cys Ala Ala Ala Leu Val
            20                  25                  30

Ala Lys Gly Ile Ser Glu Ile Ile Asn Pro Gly His Ser Asn Asp Asp
        35                  40                  45

Lys Ala Ala Arg Asp Ile Val Ser Arg Leu Gly Ala Arg Leu Glu Asp
    50                  55                  60

Gln Pro Asp Gly Ser Leu Gln Ile Thr Ser Glu Gly Val Lys Pro Val
65                  70                  75                  80

Ala Pro Phe Ile Asp Cys Gly Glu Ser Gly Leu Ser Ile Arg Met Phe
                85                  90                  95

Thr Pro Ile Val Ala Leu Ser Lys Glu Val Thr Ile Lys Gly Ser
            100                 105                 110

Gly Ser Leu Val Thr Arg Pro Met Asp Phe Phe Asp Glu Ile Leu Pro
        115                 120                 125

-continued

```
His Leu Gly Val Lys Val Lys Ser Asn Gln Gly Lys Leu Pro Leu Val
            130                 135                 140

Ile Gln Gly Pro Leu Lys Pro Ala Asp Val Thr Val Asp Gly Ser Leu
145                 150                 155                 160

Ser Ser Gln Phe Leu Thr Gly Leu Leu Leu Ala Tyr Ala Ala Ala Asp
                165                 170                 175

Ala Ser Asp Val Ala Ile Lys Val Thr Asn Leu Lys Ser Arg Pro Tyr
                180                 185                 190

Ile Asp Leu Thr Leu Asp Val Met Lys Arg Phe Gly Leu Lys Thr Pro
            195                 200                 205

Glu Asn Arg Asn Tyr Glu Glu Phe Tyr Phe Lys Ala Gly Asn Val Tyr
    210                 215                 220

Asp Glu Thr Lys Met Gln Arg Tyr Thr Val Glu Gly Asp Trp Ser Gly
225                 230                 235                 240

Gly Ala Phe Leu Leu Val Ala Gly Ala Ile Ala Gly Pro Ile Thr Val
                245                 250                 255

Arg Gly Leu Asp Ile Ala Ser Thr Gln Ala Asp Lys Ala Ile Val Gln
                260                 265                 270

Ala Leu Met Ser Ala Asn Ala Gly Ile Ala Ile Asp Ala Lys Glu Ile
            275                 280                 285

Lys Leu His Pro Ala Asp Leu Asn Ala Phe Glu Phe Asp Ala Thr Asp
    290                 295                 300

Cys Pro Asp Leu Phe Pro Pro Leu Val Ala Leu Ala Ser Tyr Cys Lys
305                 310                 315                 320

Gly Glu Thr Lys Ile Lys Gly Val Ser Arg Leu Ala His Lys Glu Ser
                325                 330                 335

Asp Arg Gly Leu Thr Leu Gln Asp Glu Phe Gly Lys Met Gly Val Glu
            340                 345                 350

Ile His Leu Glu Gly Asp Leu Met Arg Val Ile Gly Gly Lys Gly Val
        355                 360                 365

Lys Gly Ala Glu Val Ser Ser Arg His Asp His Arg Ile Ala Met Ala
    370                 375                 380

Cys Ala Val Ala Ala Leu Lys Ala Val Gly Glu Thr Thr Ile Glu His
385                 390                 395                 400

Ala Glu Ala Val Asn Lys Ser Tyr Pro Asp Phe Tyr Ser Asp Leu Lys
                405                 410                 415

Gln Leu Gly Gly Val Val Ser Leu Asn His Gln Phe Asn Phe Ser
            420                 425                 430

<210> SEQ ID NO 7
<211> LENGTH: 13066
<212> TYPE: DNA
<213> ORGANISM: Sulfolobus solfataricus
<220> FEATURE:
<221> NAME/KEY: CODING_REGION
<222> LOCATION: (10578)..(11822)

<400> SEQUENCE: 7
ctgcagtatt tctaactgtc attaaatcgt tggttttgt  aactctcatc tttattacaa      60
tctcaaactc tttgccttct actttgcttt caattgacat tccttctggc aaatttacat    120
catcaacttt taaacttctt ataaatagtt ctgcatcctt atattccgat gagattctta    180
actctatcat caatttttaat caatccttct ttctttactg acggaataaa aaatctacta    240
gtgaaaagtc tatcattgtc tctgattact atcattttat ctctcctat  ttttttgtaac    300 tgtaacaata ttatttgtgc taagagagga gaagtgagat tagatgtctc aacaatataa    360
```

```
tatgactgtt tattttcaat agaattgatt gagaatccct tggagagagt ttgcctaaat      420
ctactaatta atgcctctgc ataagaggat gacaggacaa actgtaagat ctcattactg      480
ccaatagtat caaacgaata aattaaagag aatgccaact ctaatatatc ataatcaaga      540
taaaaaaatc tatccgtaat tatatcatcc ctagtgaatt ttggatttc tttcacaata       600 gtagaaatta ttctgaaaag taatgtattt agctgactct cattcaaatc ttctaatttc      660
gatatctcac tagcgtttac ctctcttatg agacttatgg cattttctct attgccagat      720
atgccaggta tataaggatc tagagaaaac attaacgata aaaaggctgg taaagtttta      780
tatgcaggaa ttttcagatt ttttcgata gtcatatcaa atttctccat ttcccttatt       840
gtctctaatt cccattcgga aagtgatctt ctgtctaata ttgtagacgt tataatacaa      900
ctaacaattg gcaagacatc ttcagcagtt ataggtaaat atgaacaaaa ggaattctga      960
cccaagaaat attttttctt attatctatt atccatttcc cgttagcgtc aagtctaatt     1020
tgtgtttcac attcttctgg aatgaacgaa agagtgaaag aattcttagt attttggaa     1080 ataataaatg aaaataggat aggctctata gaatagtacg cagataaaca caaattatcc     1140
ttagaataca cattcctaac tacttcccct atttcttgat tattcggctc tcctaagaat     1200
acttccatta ctatctcttt agaatttctt ttgaccattt tttaagctct tcaaagctca     1260
tatccttaaa gaaatagat ccaagcaagt ttgatataat atagttcaat cttgtagcaa     1320
agacgtaaga gggatttaaa atattgata acgctaattc tcccactatt gctgcagatg     1380
gtatcggtat aatatagat acttggtata aaaagagat aaaaattgac aagaaaatat     1440
tatgtgttac ataataaaaa taacctccat ataaggcaaa actaaatata tcaatcatga     1500
tataaattac aaaatccttt gtggttcctt gcttaaggta atatttaaat tccatataat     1560
ctgtaacaat tcgttccatt ttaactatct aaagataaa ttgttcaatt ttatttactt      1620
tatcatgttg caagtaaaaa tacgacaatg ctcctatcca tccagctatg ttaaataata     1680
cgactagaat gaatacaaat tctaatgggt taaaaaagaa tggcagcagt aaaatatagc     1740
ccaaacatat tgcgagcaca tctatggatc ctataagaat agagtagcta aacgcttgcc     1800
ttaagtttac cccatatttg ttgtaaacta aacttctaac caattcttgt ccagcccatc     1860
caggtactaa taaacctacg aagttaccta gtaatcttgc tcttaacgtt atatctactc     1920
tacgcttaat tagtaatgaa tccttaaatg atgagacgaa attctgggca gtatacgtta     1980
aaagaaaaat cagaaagaat ttgggatctt cttgtaaaac atatattata ttaatcttaa     2040
atatgtatgc atagactatg atcactataa acgaagaaa aatagctgca atgtatttct     2100
tatccattat cttccccttt tctcaaaaca tccaatacta ggatagcata aagttacatt     2160
cccaagattt ttaaacactt tgggctcatc taactcagga attttcatat tagttctaaa     2220
tattccacat ttaggtttac ttatcttttg atatagaaaa ggatactcat ttagaacgca     2280
tgtcttacat tgtgagttct tctcgatgtt aattctctca atttttaatt ctctagaatc     2340
tatatagaat aatgaataat ccggattgcc tctcaagtga ttaagcatta agttaacttg     2400
aagtgtagct gttaattcta ctattagtgg agtagttcca ataacatcac atgaattccc     2460
aatttcgtct tgatctgaat agtcaataaa acaagataaa caggaggttt gactagggtc     2520 tatcagtta gcagaaccgt attccaccatt aattcctcca tatattagga ttttccctaa     2580
ttttactata gcatcattta acaatagctt gtagtacaag ctgtctaatg catcgaacac     2640
gtaatcctta tcagaaatta gcctctcgac gttctcctcg tcgagtatat ctataatata     2700
attaattttg attgaagaat ttataaggga tattttttta gcgcaaactt cagctttagg     2760
```

```
tttgcctaca tcattttcat caaataaatg gaccctatgt agattagtta tatctaccac    2820
atctgcatct actatagtta actctttaac tcctagccta gctagcaact ctgcaacggc    2880
agtacctaaa gctccacagc ctgcaattaa tatctttaac tcatttaacc tctgttgaat    2940
tcctaatcct aaaactatta gttgcctaga atatctttcc acaagattat aatgtagaat    3000 aatcttaaa aataagtgtt gcctactaaa agtggggatt gatattgttc caatggaaaa     3060
aggtggaggg agtgatggaa ctccaatatc aatagaggaa ttggacaagt taagacaagt    3120
agctgaaaag gcaagaagaa atgtaataaa aatgctattt tatgatcaaa caatacatgt    3180
gggatcgtcc ctaagtagca tagagatatt aactacgtta atattcaagc atataaggac    3240
ggattcaagc ttagtgaata aagactggct tattttaagt aaaggccatg cagcgccagc    3300
tctttatgcc gttttagctg aaaaaggtta cataaaagaa gaggaacttt ggagaataca    3360
agatataacg ggattattac aagggcatcc agaaactttt attcccggtg tagatatgtc    3420
gactggtagt ttagggcaag gtttgagctt tggaataggg gttgctactg gtataaagat    3480
ggccaacggc actggaagag tatatgtcat aatgggtgat ggtgaacagg atgagggaga    3540
aatatgggag gctatgacgc atgcagtagt tagaaatctt gataacttaa ttgcatttat    3600
agagatgaac aatttccagc ttgatggttc aacagatgag ataaaaccaa gaacttctt    3660 acctaaggta tgggaagcag taggttggaa agtattaaac tgcgatgggc atgatttcat    3720
tagtattact aatgcagtta acgaggcata aaggcaagc aagcccgtag taatattcgc     3780
taagactgta agaggaaagg ggtttcctcc aatagaaaat acccataaac agaggtccag    3840
tccagatgat gcaaggaaat atttactcaa tgcgtgaaac cttcggaagg ctattagcag    3900
acctagggga taagaacaag gatctagtcg tgataactgc agatgtagga gactctacca    3960
gagcgctata ctttagagag aagtttaagg atagatactt taatgtaggc atagcagagc    4020
aagatatggt gaattttgct gctggcttgg ctgctgtagg aaaaaagccc gctatagtta    4080
actttggaat gttcttaatg agagcgtggg agcagataag aaatagtata gctagaatga    4140
atctagacgt caagatgttt gtaacacaca ccggatacag tgaccacggt gatggttcga    4200
gtcatcaagt tctcgaagat atagcgctaa tgcgtgtatt accaaacatg aaagtagtag    4260
taccagcaga tcctaaggat attgaaagaa gcttaccagt tataattaat gaggaagggg    4320
gtccattgta ttataggata ggtagagaat attcaccacc aatcactata ggacaagaat    4380
acgaattcaa gattggtaaa gcttatgtga ttaaggatgg gagtgactta gccataatag    4440
gagcaggcgt tgttttgtgg gatgcactaa aggcggctga agaattagag aaattaggaa    4500
ttagcgtagc agttataaat ttattctcaa taaagcctat tgacgaaaat acaatagaat    4560
attatgctag aaaggctggt aagataatta ctattgagga acatagcata tatggaggta    4620
ttggttctgc cgttgcagag gttacggcta ggcgttatcc agtacccata agatttgtag    4680
gtgctacgac ttttgaagat ctgctagaa gccaaaggga tctactagat tactataata    4740
taaactataa aacaattata agggaggcaa ttgatttatt gaagtagatg actgaagaaa    4800
taacacggct gagggaagaa atagataagg tagacgagca gttagtaaag ttactctcat    4860
atagattaga attatctaga aaaatagggaaagctaagtc gaattctaat ataagtgtta    4920
ctgacgagaa tagggaaatg aaagttagag aaaaatggat tgctaacgca aaaaagtata    4980
atattccaaa tagtctggtt gaatctatat tgcctttgat ttttttcttat tctaaactag    5040 ttcagattaa cccaggagag aaagaaagag tagtaatata tggatatggc ggaatggcta    5100
aatcgatcgt ttctattctt tcattagctg ggcatgaagt atcgattact ggaagagatt    5160
```

```
taagtaaagc ggagatgtta gctaatcaat ttaaatgtgt aagtatgtcc ttattaaaag    5220
caatagattg gggggatata attatatttg caatacctcc tagtgcaata ttaaataatt    5280
ccgatgaatt attttcaaag gcacttaaag ataagattgt tatggatatt agttcttcta    5340
aatttaaaat atttggcttc ctagaagaat tatctaggaa actagagttt aggtatattt    5400
ctacacatcc acttttcggt cctattgaat accctattgg agagagagtt gtaattatac    5460
cttccaaaac tagttctaat gatgatgtca tgaaggtgga gaatttctgg aggaaaagtg    5520
gtttagtacc cgtcataact gatgttgaaa ctcatgaaaa agcaatggct attgttcaag    5580
ttctaacgca ttattatctt ctgggtttat caaacgcaat tgatacttta tcgttagagt    5640
taggtgtaga ttacagtaat ttccatacta caaactttag agaattaaac aagattttaa    5700
agcgggttaa agatctaaaa aatgtaatta ctgaaataca aaatcaaaac ccttattctt    5760
ataaagttag aaatataggt ttagaggagc ttaaaaaaat taaagaagaa ttagaaggag    5820
gtaaatagaa tgatcttata tgtccttaag gatagagctg attactctat actaatagaa    5880
aagctaaatg aaaactcagc atctttcaag atattaaacc tatatggtaa aaacttaata    5940
ttagcatggc cagatcagaa cgtgaaaggt atcattgata atagtataga aatggctgtg    6000
gaagtaaaga aaagctatgt attagctggt aatgattgga aaaagcaacc aacagtggta    6060
aatgtaaaag atgtagaaat tggaagcaaa aaggtaatag tagctgcagg tccttgtgca    6120
gtagaaaatg aagaacaagt ccttactact gctaaggctg taaaaagggc tggagcatca    6180
ttacttagag gaggggctta caaacctagg acaagtccat attccttcca aggtctcgga    6240
gaagaagggg tgaaaatctt gaggagagta ggagatgaag taggcttacc tattgtcaca    6300
gaaataatgg atacaagaga ttccaatata tttagccaat atgttgatat gatacagatt    6360
ggagccagaa acgcacagaa cttctcttta ttgaaggaag ttggaaagtt aggtaaacca    6420
gtactactta agcgaggtat gggaaataca gtagaggaat ggcttcaagc tgcagagtac    6480 atttttactag agggaaatgg caatacagta ttatgcgaaa gaggaataag aacatttgaa    6540
aagtcaacta ggtttacgtt agatataggt gggatggtag ctgctaaaact aatgacacat    6600 ttgcccatct gtgctgatcc aagtcatcct gcgggaaaaa gagaattggt acactcttta    6660
gcactagctg cagtcgctgc tggtgcggat atgttattaa ttgaagttca tccacatcca    6720
gaaaaggcat taagtgattc agagcaacaa cttacaccgg aatcattcga agttctaatg    6780
aatcgaatta gaacgctagc tagagcttta gggagagatg catgagggaa atcttagaag    6840
atatttgttg ctctgaagta agagtagtag taggagaggg atcactttca aaattatcta    6900
agattaaaga caataacgct gcagttatct attcaagaaa aattagtata gcagataaaa    6960
ttaataaata tttaccaaat gcatacttca tcccaattaa tgatggtgaa agtactaaag    7020
aattatctag tgtaatatct ttagtagaaa agctatttga aaagaatttc gataggggg    7080 attatattat aggtgttggt ggtggaacgg taactgatgt agctggtttc ttagcatcta    7140
tatatttaag aggattaaat ctgataaacg taccaacgac cttcttaggc atggtcgatg    7200
cagcaatagg gggtaagaat ggagtaaatt tcaataatat aaagaactta attggaacat    7260
tctatcaacc aagtatgata atttccgatt tagaattttt ggaaactcta ccaatagaag    7320
aactaaagaa gggattagct gaagtaatta aatatggctt aactttagat aaagaattat    7380
atgattactt gtctttaaat aaggagaaga tactaaataa agataaacaa gcattagaag    7440
atataatctt tagatctaca cttgataaac taagtattgt aaaagaagat gagagagaga    7500
ctaaaggaat acgaatagtt ctaaatttcg gccatacgat aggtcatgct atagaagctg    7560
```

```
gatcctcttt taatgttcca catggctacg ctatctctgt aggaatggtt tgtgaggcta      7620
agatggcgga agagttaggt tatgcagagg aaggagtagt agaagatgtg ttatggctat      7680
tacagattta tggtttacct tacgatatat ctcaaataga tgccccagta gatcttaaac      7740
tagcattaaa tgctattaat atggataaaa aacataggaa agatgtaatt ttgataccgt      7800
ttcctactag aataggtagc tggaaaaaag ttgaagttcc tctagatacc gtaaaggggt      7860
ttgccgaaca atgcttgaag aaataaatta tgatactaag ttattcggtc taataggtaa      7920
aaacataaag tacacgctat cccttatat tcataatttc tcatttagaa cactaggaat      7980
aaatgcagtt tatctagttt ttgatctcga cgaaatgaaa ttcaagcgta gtattagtgg      8040
gatattggaa attgcagaag gacttaatgt tacgataccg tataaggatg aagtaatgaa      8100
atatttggat aatactgata cgcactccac gagaattcaa gctgtaaata caatatataa      8160
aaaaagtggt tataacactg attatttagc aataaaaaat cttgtaagaa agaagattaa      8220
gaatgtatct ggctacgaat gttacatata tggggctgga ggtgcagcaa aagcagcagc      8280
ttttgcgtta tctgaattag gatgctctag tattagtatt gtgaatagaa caaaatcaag      8340
ggcttatgag ttagctgaat tattaaataa gaacggttat aacgcgtcaa ttaaagagaa      8400
ttgcaacatt acaaataata tacttattgt caatagcact cctaattctt ctgtagtccc      8460
agaggactgt gttaaaaaat ctgatcttgt tatagaattt gtttatagac cagttgagac      8520
tgagttaatt aaaaatgcta aaaaatatgg tatacaatat ataaacggtc tagaaatttt      8580
agtgaatcaa gctgtagaag cggagaagat atggtttaat aagagtgtgg cagatgaaaa      8640
gattatagag tatcttatg ccagggaact cgtttggtaa actatttaga ataaccactt      8700
ttggagagag ccatggtcct gcagtaggtg tagtcataga cggtgttcct gccggtttac      8760
cattaactgt tgaagatata aagttcgaat tagaatttag aagaccaggt agactatacg      8820
tttctggaag gagagaaaaa gatgagccgg aaatattaag tgggatcttt aataatagaa      8880
ctaccggatc tccaatagca gttatagtac gaaatactga tgtaatatca agtttttatg      8940
acgagattaa atataaacca agaccaggac atgcagacct tccatttata atgaaatatg      9000
gatatgaaaa ttgggattat aggggaggtg gaagagcaag tgctagagaa actgtaagta      9060
gagttatagc tggtgcagta gctaagaagt tacttatgct aacagatact tggatagctg      9120
gccatcttag aagtttaggc ccagaagagt tgagtgaaga ggtaacattt gaggaggttc      9180
tatgctcaaa atatagccca gtaagagcta gtaaaaaaga ccttgaggaa aaatatgaag      9240
cattaataaa gaaagctact caagaagggg atagctatgg cggaatagct gaagtaatag      9300
ccaagaatcc accaataggt ttaggagaac cagtctttga taagatgaaa gctgaattgg      9360
ctaaagcaat aatgtcgatc cctgctgtga tgggcttcga gtatggttta ggttttattg      9420
ctagtaaaat gaaaggaagt gaggctaatg acgagattat aagaaagaat aatagaattg      9480
gctggaagta caattacgct ggaggcattt taggtggttt aacaaatggt gaagatctta      9540
tagtgagatg tgcatttaaa cctactagct cgattagaaa gcctcaaaag accatagatt      9600
taaggaactt agaggagagt tatatttcag taattggcag acacgaccca gctgtagcaa      9660
ttaggggagt tactgttgta gaatcaatgg tagcgttaac catagtagac catgcaatgc      9720
gtgcaggagc tattccacta gttaaactta cagaggacca agctaataca atacagcaac      9780
gttgggagag gtatgtgaaa tcatgcaagc ctatggagga gtctcaatcg taaacgcact      9840
accatcttgg tatggctcat ctatggcaat caatttgaag gtaaaagtag aaattagaga      9900
aggtaagaga gtttattctc aagagagtga actaattaag accattctta attactttaa      9960
```

```
agaaaaatat tcaataccgg atattgaagt tgatattgaa tctgaacttc cacaaaagag    10020
tggactaaaa agcagtagtg cagtttctgt agccctaata gcggagattg caaagcaata    10080
tgatctaagg aatattaacc ctccaatatt atctgcgata cttttcactga aagctggagt   10140 gtcatatacc ggggcacttg atgatgcagt tgcatcatat tgtggaggaa tagcattcac    10200
ttataataag atgtttagaa tagtaaagtt agagaatctt gaggataatt tatcgatcct    10260
catattagct aagggaggga gacaaaaacc tgttaatcta aacgagctaa gaaaatatag    10320
tcacgtcttt gaagaaattt ttaagatagc acttaaggat tacttgactg ctatgaagat    10380
gaatggaata ttgattgcta atattttagg ctattcatta gaaccaatag aaattgcact    10440
gaaaaaagga gcgttagctg ccgggattag tggaaatggg ccttcatatt ttgcagtttc    10500
taagaatgga gaagaaggtc cgatatacga aagtcttaag aaatttggag atgttattat    10560
agttaggcct gtaagtcttg attgtaaaga tttatccatc aaagattagt ggaataataa    10620
aagctcctca atcaaaaagt ctagctatta ggttaatttt tctttcactt ttcactagag    10680
tatatcttca taacttagtt ctatcggaag atgttataga cgctataaaa tcagtaagag    10740
cattaggagt aaaggtaaaa aacaattctg aatttatacc tccagagaaa ttagaaatta    10800
aggagaggtt tataaaatta aaaggttccg ctactactct tagaatgctt attccaatat    10860
tagccgcaat aggcggagaa gtgacaattg atgcagatga gagtttaaga aggagacctt    10920
taaacagaat cgtacaagca ttaagtaact acggtatatc cttttcttct tacagtttgc    10980
ctttgactat cacgggaaag ttaagtagta atgagataaa gatttctggt gatgagagta    11040
gtcaatatat ttctggctta atatacgcac ttcatattct aaatggcggt agtattgaaa    11100
tattgccccc catttcatct aaaagttata ttctgcttac aatagattta tttaagagat    11160
ttggttctga tgttaagttt tatggtagta agattcatgt taatcccaat aatttggttg    11220
aatttcaagg cgaagtggcg ggagattatg gtttagcctc gttttacgcg ctttctgcat    11280
tagttagtgg tggaggaatt acaataacta atttgtggga gccgaaggaa tattttggtg    11340
atcatagtat tgttaaaata tttagtgaga tgggcgcttc cagtgaatat aaagacggta    11400
gatggtttgt caaggctaaa gataaatatt ctcccataaa aattgatata gatgacgcac    11460
ctgacctggc tatgacaatt gcgggattat ctgcaatagc ggagggaaca agtgaaatta    11520
tagggatcga aagattgagg attaaggaaa gtgatagaat tgaaagtata aggaaaatct    11580
taggattata tggtgtaggt agtgaagtaa agtataattc tattctgata ttcggaatta    11640
acaagggtat gttaaactct ccagttacag actgtttgaa tgatcacaga gttgctatga    11700
tgtcgtcagc cttagcttta gtgaatggtg gggtaattac atcagctgaa tgtgtaggta    11760
aaagtaatcc taattactgg caagatttat tatcactaaa tgcgaagatt tctattgaat    11820
gagaccatta attgtagctt cattaccaat taaaaagata gaagacttaa aacttataga    11880
aaatttttta gatgcagatc taatagaact aagacttgat tatctaagag aaagagaagt    11940
cagtttgata tctgactatt atgaattttt agataaatat aaaaagaagt taatagtaac    12000
gttaagagat aaagggggagg gaggaataaa tcaattagcg gatgaattaa agataaaaat    12060
tttaaatgaa ctctacgaga gacaatatct gtatgatata gaggtttcat tcttcaaaa     12120 atatgatata ccatacgata ataggatagt ttctgtccac tattttaatt atcttccaac    12180
tctagagaag ataaaggaaa ttgttagcaa gttttccgaa aaagcgttca gcgttaagat    12240
tgcagttcct agtctaaaag gatataagga ggtactctta cctcttcttg aatatgaaaa    12300
cgtaaccgta attccaatga gtaataattc tttagagagg atcgcagtgg gtctactggg   12360
```

```
ctcaaagtta gtttattcgt acgcaattga acctttagca caagggcaac tttactataa     12420
aaaagttatc cagattttta attatattaa cgatataaca acttcatctt tagttacttg     12480
aactctgtat acttttatag gcttttggaa agctcccttt ttaggttctc cactatatat     12540
agaaaaatga gaaagtgac  attgacatac taattcttct tttatgataa cgccatattt     12600
tgaaagatca caacctaaat gcgggcattt attatcaaaa acaaaaaatc tatctactcc     12660
tagataaaaa acgactaatt cacgtccatt aggcagtata attttctct  tttcaccagt     12720 cttaaaatca gttctactta tccttatata ctccacgact ttaattatga gctaacggag     12780
aaattaaagc aaactatgtg ttaagcataa aaataagact cttatataat aacataactt     12840
taatagagtt attgctctaa aaggtaatgc caaaattctt ccttataggt catttaatct     12900
tgataatcaa atggcaagat ttaaacataa taggtgtaga ataataaaaa ctgcttaaaa     12960
gattatgaac aaacaattta taagattggg agcaaaataa gtagattaga ggaaatcgaa     13020
gatgttagaa ataagtgagg atcttaaagc aaagcttgat tataga                    13066
```

<210> SEQ ID NO 8
<211> LENGTH: 414
<212> TYPE: PRT
<213> ORGANISM: Sulfolobus solfataricus

<400> SEQUENCE: 8

```
Met Ile Val Lys Ile Tyr Pro Ser Lys Ile Ser Gly Ile Ile Lys Ala
1               5                   10                  15

Pro Gln Ser Lys Ser Leu Ala Ile Arg Leu Ile Phe Leu Ser Leu Phe
            20                  25                  30

Thr Arg Val Tyr Leu His Asn Leu Val Leu Ser Glu Asp Val Ile Asp
        35                  40                  45

Ala Ile Lys Ser Val Arg Ala Leu Gly Val Lys Val Lys Asn Asn Ser
    50                  55                  60

Glu Phe Ile Pro Pro Glu Lys Leu Glu Ile Lys Glu Arg Phe Ile Lys
65                  70                  75                  80

Leu Lys Gly Ser Ala Thr Thr Leu Arg Met Leu Ile Pro Ile Leu Ala
                85                  90                  95

Ala Ile Gly Gly Glu Val Thr Ile Asp Ala Asp Glu Ser Leu Arg Arg
            100                 105                 110

Arg Pro Leu Asn Arg Ile Val Gln Ala Leu Ser Asn Tyr Gly Ile Ser
        115                 120                 125

Phe Ser Ser Tyr Ser Leu Pro Leu Thr Ile Thr Gly Lys Leu Ser Ser
    130                 135                 140

Asn Glu Ile Lys Ile Ser Gly Asp Glu Ser Ser Gln Tyr Ile Ser Gly
145                 150                 155                 160

Leu Ile Tyr Ala Leu His Ile Leu Asn Gly Gly Ser Ile Glu Ile Leu
                165                 170                 175

Pro Pro Ile Ser Ser Lys Ser Tyr Ile Leu Leu Thr Ile Asp Leu Phe
            180                 185                 190

Lys Arg Phe Gly Ser Asp Val Lys Phe Tyr Gly Ser Lys Ile His Val
        195                 200                 205

Asn Pro Asn Asn Leu Val Glu Phe Gln Gly Glu Val Ala Gly Asp Tyr
    210                 215                 220

Gly Leu Ala Ser Phe Tyr Ala Leu Ser Ala Leu Val Ser Gly Gly Gly
225                 230                 235                 240

Ile Thr Ile Thr Asn Leu Trp Glu Pro Lys Glu Tyr Phe Gly Asp His
                245                 250                 255
```

-continued

```
Ser Ile Val Lys Ile Phe Ser Glu Met Gly Ala Ser Ser Glu Tyr Lys
            260                 265                 270

Asp Gly Arg Trp Phe Val Lys Ala Lys Asp Lys Tyr Ser Pro Ile Lys
        275                 280                 285

Ile Asp Ile Asp Asp Ala Pro Asp Leu Ala Met Thr Ile Ala Gly Leu
    290                 295                 300

Ser Ala Ile Ala Glu Gly Thr Ser Glu Ile Ile Gly Ile Glu Arg Leu
305             310                 315                 320

Arg Ile Lys Glu Ser Asp Arg Ile Glu Ser Ile Arg Lys Ile Leu Gly
                325                 330                 335

Leu Tyr Gly Val Gly Ser Glu Val Lys Tyr Asn Ser Ile Leu Ile Phe
            340                 345                 350

Gly Ile Asn Lys Gly Met Leu Asn Ser Pro Val Thr Asp Cys Leu Asn
            355                 360                 365

Asp His Arg Val Ala Met Met Ser Ser Ala Leu Ala Leu Val Asn Gly
        370                 375                 380

Gly Val Ile Thr Ser Ala Glu Cys Val Gly Lys Ser Asn Pro Asn Tyr
385             390                 395                 400

Trp Gln Asp Leu Leu Ser Leu Asn Ala Lys Ile Ser Ile Glu
                405                 410
```

US 7,989,679 B2

METHODS AND COMPOSITIONS FOR IMPROVED ENZYME ACTIVITY IN TRANSGENIC PLANTS

RELATED APPLICATIONS

Priority is claimed to U.S. Provisional Patent Application No. 60/778,283, filed Mar. 2, 2006, and to U.S. Provisional Patent Application No. 60/891,977, filed Feb. 28, 2007, each of which is incorporated by reference in its entirety herein.

FIELD OF THE INVENTION

The present invention relates generally to molecular plant biology.

BACKGROUND OF THE INVENTION

Diurnal and seasonal variations regulate plant growth. Many of the effects of seasonal variation on plant metabolism, such as the effects of temperature change, can be attributed to altered enzymatic rates. In the case of transgenic plants, the catalytic activity of an enzyme may be further influenced by the genetic source of the transgene rather than the plant in which it is expressed (Oliver et al. (1993) *Mol. Gen. Genet.* 239:425-434).

Current commercially available transgenic plants are made tolerant of herbicides by expression of a single enzyme with a narrow functional range of effective temperature optima. See e.g., Light et al. (1999) *Weed Sci.* 47:644-650; Light et al. (2001) *Weed Sci.* 49:543-548. These limitations on herbicide resistance are well documented and have been accounted for in the formulations and application procedures of many herbicides. For example, glyphosate tolerant plants harboring the EPSP synthase enzyme CP4 are not fully tolerant of glyphosate for the duration of the growing season. If the glyphosate is used at a wrong time, the plants suffer and yields drop.

Resistance phenotypes may also be subject to additional environmental variations and/or to differential regulation of a resistance gene within plat tissues, organs, cellular compartments etc. Accordingly, methods are needed in the art to improve transgenes such that the encoded enzymes are functional across a broader spectrum of environmental conditions (e.g., temperature, soil acidity, etc.) and/or physiological conditions (e.g., pH, concentration of an enzyme substrate or cofactor, etc.). To meet this need, the present invention provides methods of expressing two or more enzymes that perform a same or similar function in a plant, wherein the two or more enzymes have difference kinetic parameters, to achieve optimal enzyme activity across a range of environmental and/or physiological conditions.

SUMMARY OF THE INVENTION

The present invention provides methods and compositions for improved enzyme activity in transgenic plants. The invention is useful as applied to plants such as agricultural plants, including both monocots and dicots.

In one aspect of the invention, transgenic plants are provided, wherein the plants have improved enzyme activity. For example, a transgenic plant may comprise at least (a) a first heterologous polynucleotide encoding a first polypeptide capable of conferring a trait of interest, and (b) a second heterologous polynucleotide encoding a second polypeptide capable of conferring said trait of interest, wherein said first and second polynucleotides are stably expressed in said plant, and wherein said plant shows said trait of interest over a broader range of a physiological or environmental condition as compared to a plant comprising either said first or second polynucleotide expressed alone and subject to said range of a physiological or environmental condition. As another example, a transgenic plant of the invention may comprise at least (a) a first heterologous polynucleotide encoding a first polypeptide capable of conferring herbicide resistance, and (b) a second heterologous polynucleotide encoding a second polypeptide capable of conferring said herbicide resistance, wherein said first and second polynucleotides are stably expressed in said plant, and wherein said plant shows said herbicide resistance over a broader range of a physiological or environmental condition as compared to a plant comprising either said first or second polynucleotide expressed alone and subject to said range of a physiological or environmental condition.

In another aspect of the invention, methods are provided for preparing transgenic plants with improved enzyme activity, which thereby confer a trait of interest to the plant. For example, such a method may comprise introducing into said plant at least (a) a first heterologous polynucleotide encoding a first polypeptide capable of conferring said trait of interest, and (b) a second heterologous polynucleotide encoding a second polypeptide capable of conferring said trait of interest, wherein said first and second polynucleotides are stably expressed in said plant, and wherein said plant shows said trait of interest over a broader spectrum of a physiological or environmental condition as compared to a plant comprising either said first or second polynucleotide expressed alone and subject to said spectrum of a physiological or environmental condition. As another example, such a method may comprise (a) providing a transgenic plant comprising a first heterologous polynucleotide encoding a first polypeptide capable of conferring said trait of interest, and (b) introducing into said plant at least a second heterologous polynucleotide encoding a second polypeptide capable of conferring said trait of interest, wherein said first and second polynucleotides are stably expressed in said plant, and wherein said plant shows said trait of interest over a broader spectrum of a physiological or environmental condition as compared to a plant comprising either said first or second polynucleotide expressed alone and subject to said spectrum of a physiological or environmental condition.

For conferring herbicide resistance to a plant, a representative method of the invention comprises introducing into said plant at least (a) a first heterologous polynucleotide encoding a first polypeptide capable of conferring resistance to said herbicide, and (b) a second heterologous polynucleotide encoding a second polypeptide capable of conferring resistance to said herbicide, wherein said first and second polynucleotides are stably expressed in said plant, and whereby said plant is herbicide resistant over a broader spectrum of a physiological or environmental condition as compared to a plant comprising either said first or second polynucleotide expressed alone and subject to said range of a physiological or environmental condition. In an additional representative method for conferring herbicide resistance to a plant, the method may comprise (a) providing a transgenic plant comprising a first heterologous polynucleotide encoding a first polypeptide capable of conferring resistance to said herbicide, and (b) introducing into said plant at least a second heterologous polynucleotide encoding a second polypeptide capable of conferring resistance to said herbicide, wherein said first and second polynucleotides are stably expressed in said plant, and whereby said plant is herbicide resistant over a broader spectrum of a physiological condition as compared to a plant comprising either said first or second polynucleotide expressed alone and subject to said range of a physiological or environmental condition.

In another aspect of the invention, methods are provided for increasing plant vigor or yield by (a) providing a plant having improved enzymatic properties as described herein; and (b) treating the plant with an effective amount of said herbicide.

DETAILED DESCRIPTION OF THE INVENTION

Figure 1:
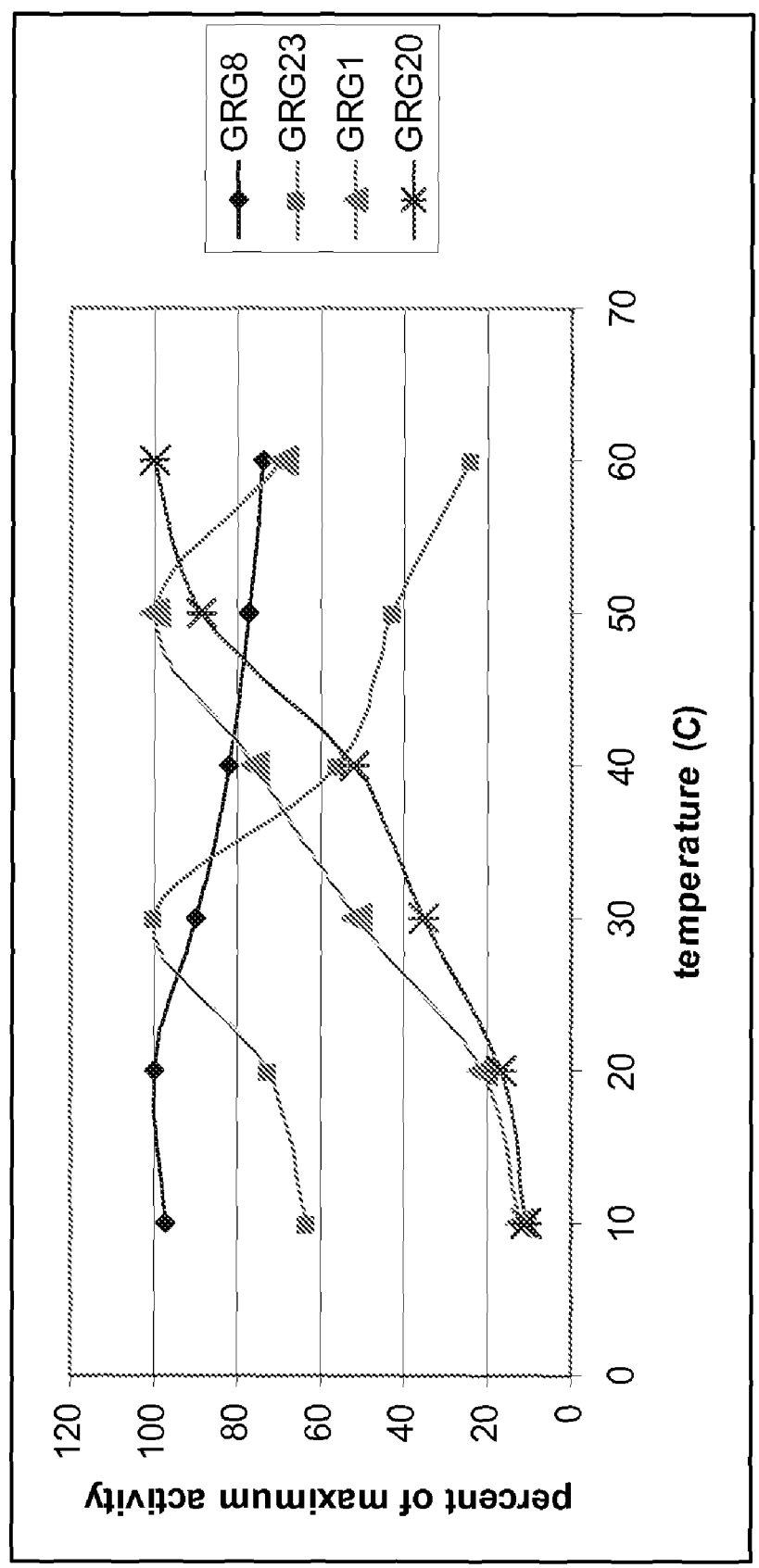
FIG. 1 is the activity of glyphosate resistant EPSP synthase enzymes derived from *Brevundomonas vesicularis* (GRG8, SEQ ID NO:2), *Arthrobacter globiformis* (GRG23, SEQ ID NO:4), Enterobacteriaceae sp. (GRG1, SEQ ID NO:6) and *Sulfolobus solfataricus* (GRG20, SEQ ID NO:8) across a broad temperature spectrum. EPSP synthase enzyme activity at each temperature is plotted as a percentage of the maximal activity.

The present invention provides methods of expressing two or more enzymes that perform a same or similar function in a plant, wherein the two or more enzymes have difference kinetic parameters, to achieve optimal enzyme activity across a range of environmental and/or physiological conditions. For example, an increase in activity of certain metabolic enzymes can result in increased or accelerated plant growth and development. Similarly, an increase in activity of an enzyme that confers resistance to herbicides, insects, or disease, enhances plant protective mechanisms to enable plant growth. Plants, plant tissues, and seeds prepared by the disclosed method are also provided.

I. Compositions

Compositions of the invention include plants or plant parts comprising a first heterologous polynucleotide encoding a first polypeptide and a second heterologous polynucleotide encoding a second polypeptide that performs a same or similar enzymatic function as the first polypeptide, and wherein expression of the first and second polynucleotides increases enzyme activity of the polypeptides over a broader range of environmental and/or physiological conditions than expression of either polynucleotide alone.

Relevant environmental and/or physiological conditions include any conditions that may result in variable activity of an enzyme of interest in a plant. The descriptors environmental and physiological are not mutually exclusive as changes in the environment can also affect physiological conditions within a plant. In addition, enzymes in different plant organs (e.g., leaves, buds, stems, flowers, fruits, tubers, rhizomes), plant tissues (e.g., dermal, ground, or vascular tissues), and/or plant cellular compartments (e.g., cytoplasm, chloroplast, mitochondria) are subject to different biochemical environments that impact optimum enzyme activity. Representative conditions include temperature, pH, concentration of an enzyme substrate or cofactor, salt concentration, concentration of free radicals or free radical donors, and concentration of an enzyme inhibitor or catalyst. The range of conditions at which each individual enzyme is active (i.e., a range of temperature or pH) can be exclusive or overlapping. For two or more enzymes which are active in an overlapping range of a environmental and/or physiological condition, the optimal enzyme activity (e.g., the percentage of maximum activity) is different among the individual enzymes such that the combined enzyme activity is increased over a broader range of conditions as compared to the enzyme activity of any one of the individual enzymes.

As used herein, an increase in enzyme activity includes any significant increase of activity or function of the polypeptide of interest, for example, an increase in the inhibition or stimulation of biological or chemical reactions within a cell or organism that can lead to enhanced or diminished metabolic activity, growth, or development. Assays to measure enzyme activity are well-known in the art. An increase in enzyme activity observed in the disclosed multiple-component expression system (i.e., plants expressing two or more polynucleotides encoding polypeptides with a same or similar function but different kinetic properties) can comprise a level of activity that is about 1% or more greater than a level of activity observed with any single component, for example, an increase of 5%, 10%, 15%, 20%, 25%, 30%, 40%, 50%, 80%, 100%, 120%, or greater. Alternatively, an increase in enzyme activity observed in the disclosed multiple-component expression system can comprise a level of activity that is about 2-fold or more greater than a level of activity observed with any single component, for example, about 5-fold or more, or about 10-fold or more, or about 25-fold or more, or about 50-fold or more, or about 100-fold or more, or about 200-fold or more, or about 500-fold or more, or about 1000-fold or more. Enzymes of a multiple component expression system may be referred to as first and second enzymes (or first, second, and third enzymes, etc.). The designations of one enzyme as a "first" enzyme and another enzyme as a "second" enzyme are merely arbitrary, the significance of the two enzymes being the differential enzymatic properties as described herein.

A broader range of environmental and/or physiological conditions, as used to describe conditions in which an enzyme of interest is active according to the disclosed methods, refers to any extension in the range of the condition, either above or below or both, within which an enzyme performs its biological function. For example, expression of two polynucleotides encoding a polypeptide of interest, wherein the first and second polypeptide have different temperature optima, resulting in an increase in enzyme activity of the polypeptide of interest over a temperature range that is at least about 1, 2, 3, 4, 5, 6, 7, 8, 9, 10, 15, 20, 25, 30, 35, 40, 45, 50, 55, 60, 65° C. or more than when either of the polynucleotides is expressed alone. In non-limiting examples, each polypeptide employed in the methods of the invention can have enzyme activity with a temperature optimum within the temperature range of about 0° C. to about 10° C., from about 10° C. to about 20° C., from about 20° C. to about 30° C., from about 30° C. to about 40° C., from about 40° C. to about 50° C., from about 50° C. to about 60° C., or from about 60° C. to about 70° C. Plants expressing the two or more polynucleotides encoding polypeptides with different temperature optima will have an elevated level of enzyme activity based upon the combined activities of the enzymes as the temperature changes throughout the day or season.

For example, a transgenic plant of the invention may comprise a plant expressing a first polypeptide having optimal enzyme activity within a temperature range of about 5° C. to about 35° C., or a plant expressing a second polypeptide having optimal enzyme activity at a higher temperature as compared to the first polypeptide and within a temperature range of about 20° C. to about 60° C. As another example, a transgenic plant of the invention may comprise a plant expressing a first polypeptide having optimal enzyme activity within a temperature range of about 10° C. to about 30° C. and a second polypeptide having optimal enzyme activity at a higher temperature as compared to the first polypeptide and within a temperature range of about 25° C. to about 50° C. Representative plants having the above-noted features include a plant expressing a first polypeptide having an amino acid sequence of SEQ ID NO:2, and a second polypeptide having an amino acid of SEQ ID NO:4, 6, or 8, and a plant expressing a first polypeptide having an amino acid sequence of SEQ ID NO:4, and a second polypeptide having an amino acid of SEQ ID NO: 6 or 8. See FIG. 1.

One non-limiting method of increasing the temperature spectrum within which an enzyme performs its biological function is to introduce into an organism one or more polynucleotides encoding an enzyme of interest derived from psychrophilic and/or thermophilic organisms. Psychrophilic organisms, such as *Bacillus globisporus* and *Shewanella* sp., are organisms that thrive at temperatures as low as or lower than 0° C. Thermophilic organisms, such as *Bacillus cadotenax, Thermus thermophilus*, and *Aquifex aeolicus*, thrive at higher temperatures, typically above 120° C. Several metabolic enzymes have been isolated from such organisms (see e.g., U.S. Pat. Nos. 6,727,084; 6,902,915; 6,921,641). U.S. Pat. No. 6,385,546 further describes a method to increase the thermophilicity (e.g., the ability to function at or above the optimal temperature for the native polypeptide) or psychrophilicity (e.g., the ability to function at or below the optimal temperature for the native polypeptide) of any enzyme by changing amino acid residues that affect the stability of the polypeptide without modifying or affecting the active or binding sites of the polypeptide. The present invention encompasses such modifications when intended to increase the desired activity of an enzyme by introducing into a plant at least two polynucleotides encoding at least two polypeptides, wherein expression of the at least two polynucleotides increases enzyme activity over a broader spectrum of temperatures than expression of either polynucleotide alone.

To address differential enzyme substrate concentrations within a plant, a two-component expression system according to the invention can comprise a first enzyme with a relatively low Km for substrate, and a relatively low catalytic rate constant ("turnover number"; Kcat), and a second enzyme having a relatively higher Km for substrate and a relatively higher catalytic rate constant as compared to the first enzyme. Optionally, the enzyme inhibition constant for a competitive inhibitor may also vary between the first and second enzymes. Plants that stably express polynucleotides encoding both enzymes will show higher levels of enzyme activity over a broader spectrum of substrate concentration than provided by either enzyme alone.

For example, the second enzyme may have an affinity for substrate that is at least about 2-fold greater than that of the first enzyme, for example, at least about 5-fold greater, or at least about 10-fold greater, or at least about 20-fold greater, or at least about 50-fold greater, or at least about 100-fold greater, or at least about 200-fold greater, or at least about 500-fold greater, or at least about 1000-fold greater, or more. As additional examples, the first enzyme may have a Km for substrate of about 1-100 µM, and the second enzyme may have a higher Km for substrate of about 30-300 µM; or the first enzyme may have a Km for substrate of about 1-100 µM, and the second enzyme may have a higher Km for substrate of about 50-500 µM. As further examples, the first enzyme may have a Km for substrate of about 1-10 µM, and the second enzyme may have a higher Km for substrate of about 5-50 µM; or the first enzyme may have a Km for substrate of about 5-10 µM, and the second enzyme may have a higher Km for substrate of about 10-50 µM; or the first enzyme may have a Km for substrate of about 5-10 µM, and the second enzyme may have a higher Km for substrate of about 15-30 µM. Relevant Km values will depend on the particular enzyme and substrate of interest, and enzyme pairs having the differential Km values as described herein can be readily identified by one of skill in the art.

Similarly, the second enzyme may have a higher catalytic rate that is increased by at least about 2-fold greater than that of the first enzyme, for example, at least about 5-fold greater, or at least about 10-fold greater, or at least about 20-fold greater, or at least about 50-fold greater, or at least about 100-fold greater, or at least about 200-fold greater, or at least about 500-fold greater, or at least about 1000-fold greater, or more. Relevant Kcat values will depend on the particular enzyme and substrate of interest, and enzyme pairs having the differential Kcat values as described herein can be readily identified by one of skill in the art.

As a specific example, two or more polynucleotides encoding an EPSP synthase can be used to confer herbicide resistance across a broader range of substrate conditions than either EPSP alone. EPSP synthase is involved in the penultimate step in the shikimic acid pathway for the biosynthesis of aromatic amino acids and many secondary metabolites, including tetrahydrofolate, ubiquinone and vitamin K (Gruys et al. (1999) *Inhibitors of Tryptophan, Phenylalanine, and Tyrosine Biosynthesis as Herbicides*, Dekker, New York). EPSP synthase converts phosphoenolpyruvic acid (PEP) and 3-phosphoshikimic acid (S3P) to 5-enolpyruvyl-3-phosphoshikimic acid (Amrhein et al. (1980) *Plant Physiol*. 66:830-834). To achieve optimal EPSP activity, a two-component expression system according to the invention can comprise a first EPSP enzyme with a substantially low Km for PEP (e.g., less than about 1 µM) and a high Ki for glyphosate (e.g., 200 µM), and a second EPSP enzyme with a more modest Km for PEP (e.g., about 40 µM) and a higher Ki for glyphosate (e.g., greater than about 2 mM). Plants that stably express polynucleotides encoding both EPSP synthases will show high levels of EPSP synthase activity over a broader spectrum of substrate concentration than provided by either enzyme alone.

For example, expression of two polynucleotides encoding a polypeptide of interest, wherein the first and second polypeptide have different Km and Kcat, can result in an increase in enzyme activity of the polypeptide of interest over a range of substrate concentration that is at least about 2-fold greater than when either of the polynucleotides is expressed alone, for example at least about 5-fold greater, or at least 10-fold greater, or at least about 25-fold greater, or at least about 50-fold greater, or at least about 100-fold greater. Similarly, the multiple-component expression system of the invention similarly provides for broadening of an effective range of enzyme activity limited by concentration of a cofactor, concentration of free radicals or free radical donors, concentration of an enzyme inhibitor or catalyst, or maximal catalytic rate.

Enzyme activity can also be regulated by differential pH in plant parts, plant tissues, and plant cellular compartments. In particular $H^+/K^+$ and/or $H^+/Na^+$ pumps maintain a higher pH in the chloroplast stroma (approximately pH 8.0) when compared to the cytoplasm (approximately pH 7.0-7.5). Alkalization of the chloroplast stroma is light-induced and allows for efficient function of photosynthetic carbon reduction cycle enzymes. See Wu et al. (1992) *Plant Physiol.* 98:666-672. For expression of heterologous enzymes in chloroplast, enzymes having optimal activity at elevated pH will be more effective in conferring the trait of interest. Several polypeptides conferring herbicide resistance are encoded in the chloroplast (e.g., the protein conferring atrazine resistance), or are encoded in the nuclear genome but function within chloroplasts (e.g., enol-pyruvylshikimate-phosphate synthase, which confers resistance to glyphosate) or mitochondria (e.g., aryl acylamidase, which confers resistance to propanil). See Della-Cioppa et al. (1986) *Proc. Natl. Acad. Sci. USA* 83, 6873-6877; Daniell et al. (1981) *Weed Res.* 21, 171-177; Gaynor et al. (1983) *Plant Physiol.* 72, 80-85. Furthermore, enzymes with varied pH optima are useful in different compartments and may confer superior properties to plants. For example, it is known in the art that the toxicity of glufosinate herbicides is due, at least in part, to inhibition of glutamine synthases ('GS's) in both cytoplasm and chloroplasts. Thus, development of plants expressing multiple glufosinate resistant GS's with differing pH optima (i.e., optimized for the pH environment of cytoplasm and alternatively chloroplast) can confer superior resistance to glufosinate by achieving maximal reaction rate in each cellular compartment. Other enzymes may also benefit from expression in multiple cellular compartments, and thus make use of the invention.

The multi-enzyme expression system of the present invention provides improved enzyme activity over a broader range of temperature as compared to the individual enzymes of the combined expression system. The pH optima of the two or more enzymes of a multi-enzyme expression system can vary as described herein above with respect to fold or percentage differences of an environmental and/or physiological condition. For example, a transgenic plant prepared as described herein may comprise a first polypeptide having optimal enzyme activity within a pH range of about pH 4.0 to about pH 6.5, and a second polypeptide having optimal enzyme activity at a higher pH as compared to the first polypeptide and within the range from about pH 6.0 to about pH 8.5. A representative plant having improved enzyme activity over a broader pH range may comprise a plant expressing a first polypeptide having an amino acid sequence of SEQ ID NO:4, and a second polypeptide having an amino acid of SEQ ID NO: 6. See Table 1.

Additional examples include a plant expressing a first polypeptide having optimal enzyme activity within a pH range of about pH 5.0 to about pH 5.5, and a second polypeptide having optimal enzyme activity at a higher pH as compared to the first polypeptide; a plant expressing a first polypeptide having optimal enzyme activity within a pH range of about pH 5.5 to about pH 6.0, and a second polypeptide having optimal enzyme activity at a higher pH as compared to the first polypeptide; a plant expressing a first polypeptide having optimal enzyme activity within a pH range of about pH 6.0 to about pH 6.5, and a second polypeptide having optimal enzyme activity at a higher pH as compared to the first polypeptide; a plant expressing a first polypeptide having optimal enzyme activity within a pH range of about pH 6.5 to about pH 7.0, and a second polypeptide having optimal enzyme activity at a higher pH as compared to the first polypeptide; a plant expressing a first polypeptide having optimal enzyme activity within a pH range of about pH 7.0 to about pH 7.5, and a second polypeptide having optimal enzyme activity at a higher pH as compared to the first polypeptide; a plant expressing a first polypeptide having optimal enzyme activity within a pH range of about pH 7.5 to about pH 8.0, and a second polypeptide having optimal enzyme activity at a higher pH as compared to the first polypeptide; and a plant expressing a first polypeptide having optimal enzyme activity within a pH range of about pH 8.0 to about pH 8.5, and a second polypeptide having optimal enzyme activity at a higher pH as compared to the first polypeptide.

Enzyme activity can also be strongly affected by salt concentration. It is known in the art that plant cells in different plant tissues are subject to large variations in salt concentration. These conditions can vary with environmental conditions. For example, stoma cells have widely varying intracellular salt levels depending on environmental conditions. Thus, the multi-enzyme expression methods of the invention are useful for generating plants with improved enzyme activity over a broader range of physiological salt concentrations than a single enzyme alone. For example, transgenic plants of the invention may comprise a first polypeptide having optimal enzyme activity within a salt concentration range of about 50 mM to 150 mM, and a said second polypeptide having optimal enzyme activity at a higher salt concentration as compared to the first polypeptide and within a range from about 100 mM to 200 mM. A representative plant having improved enzyme activity over a broader pH range may comprise a plant expressing a first polypeptide having an amino acid sequence of SEQ ID NO:4, and a second polypeptide having an amino acid of SEQ ID NO: 6. See Table 11 and FIG. 2. Additional examples include plants expressing a first polypeptide and a second polypeptide, wherein the second enzyme has optimal activity at a salt concentration that is at least about 2-fold greater than a salt concentration at which the first enzyme shows optimal activity, for example, at least about 5-fold greater, or at least about 10-fold greater, or at least about 20-fold greater, or at least about 50-fold greater, or at least about 100-fold greater, or at least about 200-fold greater, or at least about 500-fold greater, or at least about 1000-fold greater.

It may also be advantageous to express herbicide resistance genes in both cytoplasm and organelles. For example, rice plants have a robust capability for nitrogen utilization when glutamine synthetase (GS) is expressed in both cytoplasm and chloroplast. See Sun et al. (2005) *J. Plant Physiol. Mol. Biol.*

31(5): 492-498. GS is the target for the herbicide glufosinate, suggesting that mechanisms for glufosinate tolerance will be more effective if carried out in both subcellular compartments. The methods disclosed in the instant application can be used to optimally express a first and second polynucleotide encoding first and second polypeptides having optimal activities in the different pH and/or salt environments of the chloroplast and cytoplasm, respectively.

The expression of genes conferring traits of interest in chloroplasts, or in chloroplasts as well as cytoplasm, is also useful in other instances, including for example, to improve production of essential amino acids in grains (see e.g., U.S. Pat. Nos. 7,026,527 and 7,071,383); to regulate photosynthetic pathways, to regulate synthesis of lipids and plant growth regulatory hormones; to enhance a plant's ability to respond to stress conditions such as ultraviolet AB radiation, extreme temperatures, infection and/or high doses of irradiation; (see e.g. U.S. Pat. No. 6,781,034); to modulate carbon allocation and starch synthesis (see e.g., U.S. Pat. No. 6,716,474). See also Mullet, J. E. (1988) *Ann. Rev. Plant Physiol. Plant Mol Biol.* 39:475-502.

The methods of the instant invention can further be combined with methods of targeting proteins to the desired subcellular locations, such as cytoplasm, chloroplasts, and mitochondria. Thus, a heterologous polypeptide, which is optimized as disclosed herein for elevated activity in the alkaline environment of the chloroplast stroma, can further comprise a chloroplast transit peptide, as is known in the art. See e.g., U.S. Pat. No. 6,130,366 and disclosure entitled "Polynucleotide Constructs" herein below. Alternatively, the polynucleotides encoding polypeptides of interest may be stably integrated into an organelle genome. For example, representative techniques for transforming chloroplasts are described in U.S. Pat. No. 6,642,053. Polynucleotides expressed in plant organelles may also comprise promoters with specific and/or elevated expression in organelles, for example, as described in U.S. Pat. Nos. 4,710,461 and 5,391,725. See also, disclosure entitled "Polynucleotide Constructs" herein below.

I.A. Traits

Methods and compositions can be used to broaden the range of environmental and/or physiological conditions at which any enzyme of interest is active. Representative desired traits include improved crop yield; insect resistance; tolerance to broad-spectrum herbicides; resistance to diseases caused by viruses, bacteria, fungi, and worms; and enhancement of mechanisms for protection from environmental stresses such as heat, cold, drought, and high salt concentration. Additional desired traits include output traits that benefit consumers, for example, nutritionally enhanced foods that contain more starch or protein, more vitamins, more antioxidants, and/or fewer trans-fatty acids; foods with improved taste, increased shelf-life, and better ripening characteristics; trees that make it possible to produce paper with less environmental damage; nicotine-free tobacco; ornamental flowers with new colors, fragrances, and increased longevity; etc. Still further, desirable traits that may be used in accordance with the invention include gene products produced in plants as a means for manufacturing, for example, therapeutic proteins for disease treatment and vaccination; textile fibers; biodegradable plastics; oils for use in paints, detergents, and lubricants; etc. Enzyme activity relevant to any of the above-noted traits, or any other desirable plant trait, can be optimized by selection of multiple polynucleotides having different kinetic properties, as described herein.

In one aspect of the invention, the polynucleotide of interest encodes a polypeptide capable of conferring herbicide resistance, i.e., an ability to tolerate a higher concentration of an herbicide, or to tolerate a certain concentration of an herbicide for a longer period of time than plants that are not tolerant or resistant to the herbicide. Techniques for measuring herbicide resistance activity are well known in the art. See e.g. U.S. Pat. Nos. 4,535,060 and 5,188,642, each of which is herein incorporated by reference in their entirety.

Herbicides for which several resistant or tolerant transgenes have been identified include, but are not limited to, the following:

(a) An herbicide of interest includes one that inhibits the growing point or meristem, such as an imidazolinone or a sulfonylurea. Exemplary polynucleotides that impart herbicide resistance to this class of herbicides include mutant ALS and AHAS enzymes as described, for example, by Lee et al. (1988) *EMBO J.* 7:1241, and Miki et al. (1990) *Theor. Appl. Genet.* 80: 449, respectively. See also, U.S. Pat. Nos. 5,198,599; 5,605,011; 5,013,659; 5,141,870; 5,767,361; 5,731,180; 5,304,732; 4,761,373; 5,331,107; 5,928,937; and 5,378,824; and PCT International Publication No. WO 96/33270, each of which is incorporated herein by reference.

(b) Additional herbicides of interest include glyphosate (resistance imparted by mutant 5-enolpyruvl-3-phosphikimate synthase (EPSP synthase) and aroA genes). See e.g. U.S. Pat. No. 4,940,835, which discloses the polynucleotide of a form of EPSP synthase which can confer glyphosate resistance. U.S. Pat. No. 5,627,061 also describes genes encoding EPSP synthase enzymes. See also U.S. Pat. Nos. 6,566,587; 6,338,961; 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; RE 36,449; RE 37,287 E; and 5,491,288; PCT International Publication No. WO 01/66704; European Patent Application Publication Nos. EP1173581A and EP1173580A; and European Patent No. EP1173582, each of which is incorporated herein by reference. Additional representative EPSP polynucleotides are set forth as SEQ ID NOs: 1, 3, 5, and 7, which encode EPSP polypeptides set forth as SEQ ID NOs: 2, 4, 6, and 8, respectively.

Glyphosate resistance is also imparted to plants that express a gene encoding a glyphosate oxidoreductase enzyme as described more fully in U.S. Pat. Nos. 5,776,760 and 5,463,175, which are incorporated herein by reference. In addition, glyphosate resistance can be imparted to plants by the over expression of polynucleotides encoding glyphosate N-acetyltransferase. See e.g., U.S. Patent Application Publication Nos. 20040082770 and PCT International Publication No. WO 01/46227. A DNA molecule encoding a mutant aroA gene, which also confers glyphosate resistance, can be obtained under American Type Culture Collection (ATCC) Accession No. 39256, and the polynucleotide of the mutant gene is disclosed in U.S. Pat. No. 4,769,061.

EPSP synthases have been isolated from plants, bacteria and fungi, including *E. coli* (Duncan et al. (1984) *FEBS Lett.* 170:59-63), *Staphylococcus aureus* (Horsburgh et al. (1996) *Microbiology* 142 (Part 10):2943-2950), *Streptococcus pneumoniae* (Du et al. (2000) *Eur. J. Biochem.* 267(1):222-227) and *Salmonella typhi* (Chatfield et al. (1990) *Nucleic Acids Res.* 18(20):6133). EPSP synthase sequences have been characterized and residues frequently conserved in this class of polypeptides have been identified. For example, Lys-22, Arg-124, Asp-313, Arg-344, Arg-386, and Lys-411, are conserved residues of the EPSP synthase from *E. coli* (Schönbrunn et al. (2001) *Proc. Natl. Acad. Sci. U.S.A.* 98:1376-1380). Additional residues that influence EPSP synthase activity also include Arg-100, Asp-242, and Asp-384 (Selvapandiyan et al.

(1995) *FEBS Letters* 374:253-256). Arg-27 has been shown to bind to S3P (Shuttleworth et al. (1999) *Biochemistry* 38:296-302).

EPSP synthase is the target of the herbicide glyphosate, i.e., any herbicidal form of N-phosphonomethylglycine (including any salt thereof) and active derivatives thereof that result in the production of the glyphosate anion in planta. Inhibition of EPSP synthase by glyphosate has been shown to proceed through the formation of an EPSP synthase-S3P-glyphosate ternary complex and the binding is ordered with glyphosate binding to the enzyme only after the formation of a binary EPSP synthase-S3P complex. Binding of glyphosate to EPSP synthase has been shown to be competitive with PEP and uncompetitive with respect to S3P (Kishore et al. (1988) *Ann. Rev. Biochem.* 57:627-663). By binding to EPSP synthase, glyphosate shuts down the shikimic acid pathway, thereby leading to a depletion of aromatic amino acid biosynthesis and death or severe growth reduction of the plant.

Glyphosate-resistant EPSP synthase polypeptides have been identified and used to increase glyphosate tolerance in plants. Glyphosate resistance polypeptides confer upon a cell an ability to tolerate a higher concentration of glyphosate than cells that do not express the polypeptide, or to tolerate a certain concentration of glyphosate for a longer time than cells that do not express the polypeptide. Tolerance refers to an ability to survive, or to carry out essential cellular functions such as protein synthesis and respiration in a manner that is not readily discernable from untreated cells. An example of a naturally-occurring glyphosate-resistant EPSP synthase includes the bacterial gene from *Agrobacterium tumefacians* strain CP4 which has been used to confer herbicide resistance on plant cells following expression in plants. Mutated EPSP synthase polypeptides have been identified through random mutagenesis and selection for herbicide resistance, including a mutated EPSP synthase from *Salmonella typhimurium* strain CT7 that confers glyphosate resistance in bacterial cells, and confers glyphosate resistance on plant cells (U.S. Pat. Nos. 4,535,060; 4,769,061; and 5,094,945 and U.S. Appl. Nos. 60/669,686 and 20040177399). These enzymes contain amino acid substitutions in their active sites that prevent the binding of glyphosate without affecting binding by PEP or S3P. Mutations that occur in the hinge region between the two globular domains of EPSP synthase have been shown to alter the binding affinity of glyphosate but not PEP (He et al. (2003) *Biosci. Biotechnol. Biochem.* 67(6): 1405-1409). Therefore, such enzymes have high catalytic activity, even in the presence of glyphosate.

In one aspect of the invention, the present invention provides transgenic plants having two or more polypeptides conferring glyphosate resistance, for example, two or more glyphosate resistant EPSP synthase polypeptides, wherein the plants have an increased resistance to glyphosate and/or an increased yield over a broader range of environmental and/or physiological conditions than when only one of the polypeptides is expressed in the plant. For example, plants expressing two or more EPSP synthase polypeptides have a broader temperature spectrum of resistance to glyphosate or increased yield of about 1, 2, 3, 4, 5, 6, 7, 8, 9, 10, 11, 12, 13, 14, 15, 20, or 25, 35, 45, 55, 65° C. or greater than when either EPSP synthase polypeptides are expressed alone. Also provided are plants expressing two or more EPSP synthase polypeptides, wherein at least one of the two EPSP synthase polypeptides is active between about 0° C. to about 10° C., about 10° C. to about 20° C., about 20° C. to about 30° C., about 30° C. to about 40° C., about 40° C. to about 50° C., about 50° C. to about 60° C., or about 60° C. to about 70° C.

A variety of techniques can be used to assay EPSP synthase activity. For example, Lewendon et al. (1983) *Biochem J.* 213:187-91 describes two assays which couple the EPSP synthase reaction with other enzymes which produced detectable products. In the forward direction, EPSP synthase can be coupled with chorismate synthase, the enzyme in the shikimate acid pathway which converts EPSP to chorismate; as EPSP synthase produces EPSP, chorismate synthase can convert EPSP to chorismate which can be detected at 275 nm. Since EPSP synthase can also proceed in the reverse direction, activity can also be assayed with coupling to pyruvate kinase and lactate dehydrogenase which oxidize NADH in the breakdown of pyruvate, allowing the detection of NADH loss at 340 nm which corresponds to pyruvate evolution by EPSP synthase. EPSP synthase activity can also be assayed by measuring an increase in resistance of a plant to glyphosate when glyphosate-resistant EPSP synthase is present, or by measuring an increase in plant yield when glyphosate-sensitive and/or -tolerant EPSP synthase is expressed.

An increase in activity of glyphosate-sensitive or glyphosate-tolerant EPSP synthase across a broader range of temperatures (such as those that span night and day in many climates, and those that extend beyond typical growing seasons in some climates) will result in increased production of metabolic components necessary for growth and development and, hence, improve plant yield. EPSP synthase sequences derived from plants (both monocots and dicots) and other microorganisms (such as bacteria, fungi or yeast) are also included in this invention. For example, glyphosate-tolerant EPSP synthase enzymes derived from *Brevundomonas vesicularis*, *Arthrobacter globiformis*, Enterobacteriaceae sp., and *Sulfolobus solfataricus* are enzymatically active at varying temperatures. Representative glyphosate resistant plants of the invention include plants expressing glyphosate-tolerant EPSP synthase polypeptides derived from at least *Brevundomonas vesicularis* and *Arthrobacter globiformis*; *Brevundomonas vesicularis* and Enterobacteriaceae sp.; *Brevundomonas vesicularis* and *Sulfolobus solfataricus*; *Arthrobacter globiformis* and Enterobacteriaceae sp.; *Arthrobacter globiformis* and *Sulfolobus solfataricus*; or Enterobacteriaceae sp. and *Sulfolobus solfataricus*. Additional plants of the invention express glyphosate-tolerant EPSP synthase polypeptides derived from at least *Brevundomonas vesicularis*, *Arthrobacter globiformis*, and Enterobacteriaceae sp.; *Brevundomonas vesicularis*, Enterobacteriaceae sp. and *Sulfolobus solfataricus*; *Arthrobacter globiformis*, Enterobacteriaceae sp., and *Sulfolobus solfataricus*; or *Brevundomonas vesicularis*, *Arthrobacter globiformis*, and *Sulfolobus solfataricus*. Still additional plants of the inventions express glyphosate tolerant EPSP synthase polypeptides derived from at least *Brevundomonas vesicularis*, *Arthrobacter globiformis*, Enterobacteriaceae sp., and *Sulfolobus solfataricus*. It is contemplated that other glyphosate-tolerant EPSP synthase polypeptides can be used in the present invention in addition to those described above, or in any combination with any number of the polypeptides described above such that EPSP synthase is active across a broader range of environmental and/or physiological conditions than expression of either EPSP synthase polypeptide alone.

As discussed in further detail herein below, variants of any known EPSP synthase enzymes or those disclosed herein can be employed in the methods and compositions of the invention. Functional variants of EPSP synthase which are tolerant to glyphosate are known. See e.g. Kishore and Shah (1988)

*Ann. Rev. Biochem.* 57:627-63; Wang et al. (2003) *J. Plant Res.* 116:455-60; and Eschenburg et al. (2002) *Planta* 216: 129-35.

(c) An herbicide that inhibits photosynthesis, such as a triazine (psbA and gs+genes) and a benzonitrile (nitrilase gene) is also of interest. Przibilla et al. (1991) *Plant Cell* 3:169 describes the transformation of *Chlamydomonas* with plasmids encoding mutant psbA genes. Polynucleotides for nitrilase genes are disclosed in U.S. Pat. No. 4,810,648 and DNA molecules containing these genes are available under ATCC Accession Nos. 53435, 67441, and 67442. Cloning and expression of DNA coding for a glutathione S-transferase is described by Hayes et al. (1992) *Biochem. J.* 285:173.

(d) Acetohydroxy acid synthase, which has been found to make plants that express this enzyme resistant to multiple types of herbicides, has been introduced into a variety of plants (see e.g., Hattori et al. (1995) *Mol. Gen. Genet.* 246: 419). Other genes that confer resistance to herbicides include: a gene encoding a chimeric polypeptide of rat cytochrome P4507A1 and yeast NADPH-cytochrome P450 oxidoreductase (Shiota et al. (1994) *Plant Physiol.* 106:17), genes for glutathione reductase and superoxide dismutase (Aono et al. (1995) *Plant Cell Physiol.* 36:1687), and genes for various phosphotransferases (Datta et al. (1992) *Plant Mol. Biol.* 20:619).

(e) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,084,155; 6,288,306; 6,282, 837; and 5,767,373; and PCT International Publication No. WO 01/12825.

(f) Additional herbicides of interest include phosphono compounds such as glufosinate (resistance provided by phosphinothricin acetyl transferase (PAT) and *Streptomyces hygroscopicus* phosphinothricin acetyl transferase (bar) genes). European Patent Application Publication No. 0333033A and U.S. Pat. No. 4,975,374 disclose polynucleotides of glutamine synthetase genes which confer resistance to herbicides such as L-phosphinothricin. The polynucleotide of a phosphinothricin acetyl transferase gene is provided in European Patent Nos. 0242246 and 0242236. De Greef et al. (1989) *BioTechnology* 7: 61 describe the production of transgenic plants that express chimeric bar genes coding for phosphinothricin acetyl transferase activity. See also U.S. Pat. Nos. 5,969,213; 5,489,520; 5,550,318; 5,874,265; 5,919,675; 5,561,236; 5,648,477; 5,646,024; 6,177,616; and 5,879,903, which are incorporated herein by reference.

(e) Additional herbicides are pyridinoxy or phenoxy proprionic acids and cycloshexones (resistance conferred by ACCase inhibitor-encoding genes). Exemplary polynucleotides conferring resistance to phenoxy proprionic acids and cycloshexones, such as sethoxydim and haloxyfop, are the Acc1-S1, Acc1-S2 and Acc1-S3 genes described by Marshall et al. (1992) *Theor. Appl. Genet.* 83: 435.

I.B. Polynucleotide and Polypeptide Variants

The present invention further contemplates variants and fragments of the herbicide resistance polynucleotides and polypeptides described herein. Various methods can be employed to modify the various polypeptides which confer resistance to an herbicide such that the new polypeptide will have the desired activity at a different temperature optimum. For example, gene shuffling or sexual PCR procedures (for example, Smith (1994) *Nature* 370:324-25; U.S. Pat. Nos. 5,837,458; 5,830,721; 5,811,238; and 5,733,731, each of which is herein incorporated by reference) can be used to identify additional polynucleotides that encode polypeptides that perform similar functions as those described herein (for example, polypeptides that confer herbicide resistance at varying temperature optima). Gene shuffling involves random fragmentation of several mutant DNAs followed by their reassembly by PCR into full length molecules. Examples of various gene shuffling procedures include, but are not limited to, assembly following DNase treatment, the staggered extension process (STEP), and random priming in vitro recombination. In the DNase mediated method, DNA segments isolated from a pool of positive mutants are cleaved into random fragments with DNaseI and subjected to multiple rounds of PCR with no added primer. The lengths of random fragments approach that of the uncleaved segment as the PCR cycles proceed, resulting in mutations in different clones becoming mixed and accumulating in some of the resulting sequences. Multiple cycles of selection and shuffling have led to the functional enhancement of several enzymes (Stemmer (1994) *Nature* 370:398-91; Stemmer (1994) *Proc. Natl. Acad. Sci. USA* 91:10747-51; Crameri et al. (1996) *Nat. Biotechnol.* 14:315-19; Zhang et al. (1997) *Proc. Natl. Acad. Sci. USA* 94:4504-09; and Crameri et al. (1997) *Nat. Biotechnol.* 15:436-38). Such procedures could be performed, for example, on polynucleotides derived from cryophilic and/or thermophilic organisms to generate polypeptides that are active at lower and higher temperature ranges, as well as those that confer a desired enzyme activity (i.e., herbicide resistance).

Fragments or biologically active portions include polypeptide fragments comprising a portion of an amino acid sequence encoding a polypeptide and that retains biological activity (i.e., herbicide resistance or EPSP synthase activity such as increased yield and/or resistance to glyphosate). A fragment of a polynucleotide may encode a biologically active portion of a polypeptide, or it may be a fragment that can be used as a hybridization probe or PCR primer using methods disclosed elsewhere herein. Polynucleotides that are fragments of a polynucleotide comprise at least about 15, 20, 50, 75, 100, 200, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950 contiguous nucleotides, or up to the number of nucleotides present in a full-length polynucleotide disclosed herein depending upon the intended use. Contiguous nucleotides are immediately adjacent to one another.

Fragments of a polynucleotide can encode polypeptide fragments that retain the biological activity of the full-length polypeptide (e.g., herbicide resistance or EPSP synthase activity such as increased yield and/or resistance to glyphosate). For example, a fragment retains a biological activity of the full-length polypeptide if it has at least about 30%, at least about 50%, at least about 70%, or at least about 80% of the activity of the full-length polypeptide.

A fragment of a polynucleotide that encodes a biologically active portion of a polypeptide of the invention can encode at least about 15, 25, 30, 50, 75, 100, 125, 150, 175, 200, 250, 300, 350, 400 contiguous amino acids, or up to the total number of amino acids present in a full-length polypeptide of the invention.

The invention also encompasses variant polynucleotides, including naturally occurring variants as well as recombinantly produced variants. For example, variants of the EPSP synthase polypeptides disclosed herein include polypeptides that differ conservatively because of the degeneracy of the genetic code, as well as those that are sufficiently identical.

Sufficiently identical polypeptides refer to polypeptides having an amino acid sequence that has at least about 60% or 65% sequence identity, about 70% or 75% sequence identity, about 80% or 85% sequence identity, about 90%, 91%, 92%, 93%, 94%, 95%, 96%, 97%, 98% or 99% sequence identity compared to a reference sequence using one of the alignment programs using standard parameters. One of skill in the art recognizes that these values can be appropriately adjusted to determine corresponding identity of polypeptides encoded by two polynucleotides by taking into account codon degeneracy, amino acid similarity, reading frame positioning, and the like. Amino acid substitutions that are made to increase the thermophilicity, psychrophilicity, or thermostability of an enzyme are also encompassed by the present invention.

To determine the percent identity of two amino acid sequences or of two polynucleotides, the sequences are aligned for optimal comparison purposes. The percent identity between the two sequences is a function of the number of identical positions shared by the sequences (i.e., percent identity=number of identical positions/total number of positions (e.g., overlapping positions)×100). The two sequences may be the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain polynucleotides homologous to herbicide resistance-encoding polynucleotides used in methods of the invention. BLAST polypeptide searches can be performed with the BLASTX program, score=50, wordlength=3, to obtain amino acid sequences homologous to polypeptide molecules expressed using the methods of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. See world wide web page ncbi.nlm.nih.gov. Another non-limiting example of a mathematical algorithm utilized for the comparison of sequences is the ClustalW algorithm (Higgins et al. (1994). *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNAIamino acid analysis software packages, such as the ALIGNX module of the vector NTi Program Suite (Informax, Inc). After alignment of amino acid sequences with ClustalW, the percent amino acid identity can be assessed. A non-limiting example of a software program useful for analysis of ClustalW alignments is GENEDOC™. GENEDOC™ (Karl Nicholas) allows assessment of amino acid (or DNA) similarity and identity between multiple polypeptides. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package. When utilizing the ALIGN program for comparing amino a PAM120 weight residue table, a gap length penalty of 12, and a gap penalty of 4 can be used.

Unless otherwise stated, GAP Version 10, which uses the algorithm of Needleman and Wunsch (1970) supra, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used, including any sequence comparison program that, for any two sequences in question, generates an alignment having identical nucleotide residue matches and an identical percent sequence identity when compared to the corresponding alignment generated by GAP Version 10.

Naturally occurring polynucleotide variants can be identified using well-known molecular biology techniques, such as polymerase chain reaction (PCR) and hybridization techniques as outlined below. Variant polynucleotides also include synthetically derived polynucleotides that have been generated, for example, by using site-directed mutagenesis but which still encode the polypeptide having the desired biological activity. Variant polypeptides encompassed by the present invention are biologically active, that is they retain the desired biological activity of the native polypeptide, i.e., herbicide resistance activity or EPSP synthase activity such as increased yield and/or resistance glyphosate. Biologically active variants have at least about 30% of the activity of the native polypeptide, for example, at least about 50%, or at least about 70%, or at least about 80%, or at least about 90%, or at least about 95%. Methods for measuring enzyme activity are specific to individual enzymes of interest.

The skilled artisan further appreciates that changes can be introduced by mutation into the polynucleotides of the invention thereby leading to changes in the amino acid sequence of the encoded polypeptides, without altering the biological activity of the polypeptides. Thus, variant isolated polynucleotides can be created by introducing one or more nucleotide substitutions, additions, or deletions into the corresponding polynucleotide disclosed herein, such that one or more amino acid substitutions, additions or deletions are introduced into the encoded polypeptide. Mutations can be introduced by standard techniques, such as site-directed mutagenesis and PCR-mediated mutagenesis, or shuffling techniques, which are described in further detail elsewhere herein. Such variant polynucleotides are also encompassed by the present invention.

For example, conservative amino acid substitutions may be made at one or more nonessential amino acid residues, i.e., a residue that can be altered from the native sequence of a polypeptide without altering the biological activity. In contrast, an essential amino acid residue is required for biological activity. A conservative amino acid substitution is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Amino acid substitutions may be made in nonconserved regions that retain function. In general, such substitutions would not be made for conserved amino acid residues, or for amino acid residues residing within a conserved motif, where such residues are essential for polypeptide activity. However, one of skill in the art would understand that functional variants may have minor conserved or nonconserved alterations in the conserved residues.

Alternatively, variant polynucleotides can be made by introducing mutations randomly along all or part of the coding sequence, such as by saturation mutagenesis, and the resultant mutants can be screened for the ability to confer herbicide resistance activity to identify mutants that retain activity. Following mutagenesis, the encoded polypeptide can be expressed recombinantly, and the activity of the polypeptide can be determined using standard assay techniques.

I.C. Expression Constructs

The polynucleotides employed in the methods and compositions of the invention may be modified to obtain or enhance expression in plant cells. The polynucleotides of the invention may be provided in expression cassettes for expression in the plant of interest. Plant expression cassettes include a DNA construct that is capable of resulting in the expression of a polynucleotide in a plant cell. The cassette can include in the 5'-3' direction of transcription, a transcriptional initiation region (i.e., promoter) operably linked to one or more polynucleotides of interest, and a translation and transcriptional termination region (i.e., termination region) functional in plants. The cassette may additionally contain at least one additional polynucleotide to be introduced into the organism, such as a selectable marker gene or the second polynucleotide of interest with different temperature optima for activity. Alternatively, the additional polynucleotide(s) can be provided on multiple expression cassettes. Such an expression cassette is provided with a plurality of restriction sites for insertion of the polynucleotide(s) to be under the transcriptional regulation of the regulatory regions.

A heterologous polynucleotide or polypeptide is one that is not endogenous to the cell or is not endogenous to the location in the native genome in which it is present, and has been added to the cell by infection, transfection, microinjection, electroporation, microprojection, or the like. For expression of a heterologous polynucleotide, such polynucleotide is operably linked to a promoter sequence that initiates and mediates its transcription. It is recognized that operably linked polynucleotides may or may not be contiguous. Where used to reference the joining of two polypeptide coding regions, operably linked polypeptides are expressed in the same reading frame.

The promoter may be any polynucleotide sequence which shows transcriptional activity in the chosen plant cells, plant parts, or plants. The promoter may be native or analogous, or foreign or heterologous, to the plant host and/or to the DNA sequence of the invention. Where the promoter is native or endogenous to the plant host, it is intended that the promoter is found in the native plant into which the promoter is introduced. Where the promoter is foreign or heterologous to the DNA sequence of the invention, the promoter is not the native or naturally occurring promoter for the operably linked DNA sequence of the invention. The promoter may be inducible or constitutive. It may be naturally-occurring, may be composed of portions of various naturally-occurring promoters, or may be partially or totally synthetic. Guidance for the design of promoters is provided by studies of promoter structure, such as that of Harley and Reynolds (1987) *Nucleic Acids Res.* 15:2343-61. Also, the location of the promoter relative to the transcription start may be optimized. See e.g. Roberts, et al. (1979) *Proc. Natl. Acad. Sci. USA*, 76:760-4. Many suitable promoters for use in plants are well known in the art.

For instance, suitable constitutive promoters for use in plants include: the promoters from plant viruses, such as the peanut chlorotic streak caulimovirus (PClSV) promoter (U.S. Pat. No. 5,850,019); the 35S promoter from cauliflower mosaic virus (CaMV) (Odell et al. (1985) *Nature* 313:810-812); promoters of Chlorella virus methyltransferase genes (U.S. Pat. No. 5,563,328) and the full-length transcript promoter from figwort mosaic virus (FMV) (U.S. Pat. No. 5,378, 619); the promoters from such genes as rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); peMU (Last et al. (1991) *Theor. Appl. Genet.* 81:581-588); MAS (Velten et al. (1984) *EMBO J.* 3:2723-2730); maize H3 histone (Lepetit et al. (1992) *Mol. Gen. Genet.* 231:276-285 and Atanassova et al. (1992) *Plant J.* 2(3):291-300); *Brassica napus* ALS3 (PCT International Publication No. WO 97/41228); and promoters of various *Agrobacterium* genes (see U.S. Pat. Nos. 4,771, 002; 5,102,796; 5,182,200; and 5,428,147).

Suitable inducible promoters for use in plants include: the promoter from the ACE1 system which responds to copper (Mett et al. (1993) *Proc. Natl. Acad. Sci. USA* 90:4567-4571); the promoter of the maize In2 gene which responds to benzenesulfonamide herbicide safeners (Hershey et al. (1991) *Mol. Gen. Genetics* 227:229-237 and Gatz et al. (1994) *Mol. Gen. Genetics* 243:32-38); and the promoter of the Tet repressor from Tn10 (Gatz et al, (1991) *Mol. Gen. Genet.* 227:229-237). Another inducible promoter for use in plants is one that responds to an inducing agent to which plants do not normally respond. An exemplary inducible promoter of this type is the inducible promoter from a steroid hormone gene, the transcriptional activity of which is induced by a glucocorticosteroid hormone (Schena et al. (1991) *Proc. Natl. Acad. Sci. USA* 88:10421) or the recent application of a chimeric transcription activator, XVE, for use in an estrogen receptor-based inducible plant expression system activated by estradiol (Zuo et al. (2000) *Plant J.*, 24:265-273). Other inducible promoters for use in plants are described in EP 332104, PCT International Publication Nos. WO 93/21334 and WO 97/06269. Promoters composed of portions of other promoters and partially or totally synthetic promoters can also be used. See e.g., Ni et al. (1995) *Plant J.* 7:661-676 and PCT International Publication No. WO 95/14098 describing such promoters for use in plants.

The promoter may include, or be modified to include, one or more enhancer elements. Promoters containing enhancer elements provide for higher levels of transcription as compared to promoters that do not include them. Suitable enhancer elements for use in plants include the PClSV enhancer element (U.S. Pat. No. 5,850,019), the CaMV 35S enhancer element (U.S. Pat. Nos. 5,106,739 and 5,164,316) and the FMV enhancer element (Maiti et al. (1997) *Transgenic Res.* 6:143-156). See also PCT International Publication No. WO 96/23898.

Often, such constructs can contain 5' and 3' untranslated regions. Such constructs may contain a 'signal sequence' or 'leader sequence' to facilitate co-translational or post-translational transport of the peptide of interest to certain intracellular structures such as the chloroplast (or other plastid), endoplasmic reticulum, or Golgi apparatus, or to be secreted. For example, the construct can be engineered to contain a signal peptide to facilitate transfer of the peptide to the endoplasmic reticulum. A signal sequence is known or suspected to result in cotranslational or post-translational peptide transport across the cell membrane. In eukaryotes, this typically involves secretion into the Golgi apparatus, with some resulting glycosylation. A leader sequence refers to any sequence that, when translated, results in an amino acid sequence sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like. Plant expression cassettes may also contain an intron, such that mRNA processing of the intron is required for expression.

A 3' untranslated region is a polynucleotide located downstream of a coding sequence. Polyadenylation signal sequences and other sequences encoding regulatory signals capable of affecting the addition of polyadenylic acid tracts to the 3' end of the mRNA precursor are 3' untranslated regions. A 5' untranslated region is a polynucleotide located upstream of a coding sequence.

Other upstream or downstream untranslated elements include enhancers. Enhancers are polynucleotides that act to increase the expression of a promoter region. Enhancers are well known in the art and include, but are not limited to, the SV40 enhancer region and the 35S enhancer element.

The termination region may be native with the transcriptional initiation region, may be native with the sequence of the present invention, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the polynucleotide(s) may be optimized for increased expression in the transformed host cell. That is, the sequences can be synthesized using host cell-preferred codons for improved expression, or may be synthesized using codons at a host-preferred codon usage frequency. Generally, the GC content of the polynucleotide will be increased. See e.g. Campbell and Gowri (1990) *Plant Physiol.* 92:1-11 for a discussion of host-preferred codon usage. Methods are known in the art for synthesizing host-preferred polynucleotides. See e.g. U.S. Pat. Nos. 6,320,100; 6,075,185; 5,380,831; and 5,436,391, U.S. Published Application Nos. 20040005600 and 20010003849, and Murray et al. (1989) *Nucleic Acids Res.* 17:477-498, herein incorporated by reference.

In one aspect of the invention, polynucleotides of interest are targeted to the chloroplast for expression. In this manner, where the polynucleotide of interest is not directly inserted into the chloroplast, the expression cassette may additionally contain a polynucleotide encoding a transit peptide to direct the nucleotide of interest to the chloroplasts. Such transit peptides are known in the art. See e.g., Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The polynucleotides of interest to be targeted to the chloroplast may be optimized for expression in the chloroplast to account for differences in codon usage between the plant nucleus and this organelle. In this manner, the polynucleotides of interest may be synthesized using chloroplast-preferred codons. See e.g., U.S. Pat. No. 5,380,831, herein incorporated by reference.

This plant expression cassette can be inserted into a plant transformation vector, which allows for the transformation of DNA into a cell. Such a molecule may consist of one or more expression cassettes, and may be organized into more than one vector DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). Vectors are polynucleotide constructs designed for transfer between different host cells. Expression vectors are a type of vector having an ability to incorporate, integrate and express heterologous DNA sequences or fragments in a foreign cell.

The plant transformation vector comprises one or more DNA vectors for achieving plant transformation. For example, it is a common practice in the art to utilize plant transformation vectors that comprise more than one contiguous DNA segment. These vectors are often referred to in the art as binary vectors. Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a polynucleotide of interest (i.e., a polynucleotide engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker sequence and the sequence of interest are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as in understood in the art (Hellens and Mullineaux (2000) *Trends in Plant Science,* 5:446-451). Several types of *Agrobacterium* strains (e.g., LBA4404, GV3101, EHA11, EHA105, etc.) can be used for plant transformation. The second plasmid vector is not necessary for introduction of polynucleotides into plants by other methods such as microprojection, microinjection, electroporation, polyethylene glycol, etc.

The present invention further provides transgenic plants comprising more than one of the polynucleotides of the invention to elevate the activity of the desired enzyme over a broad temperature spectrum. One of skill in the art recognizes that several different strategies can be utilized to generate such a plant or plant part including, but not limited to the following:

Fused enzyme. In this aspect of the invention, the first polynucleotide is positioned in the plant vector directly downstream of at least the second polynucleotide under the direction of a single promoter. Alternatively, the first and at least the second polynucleotides can be separated and put under the direction of different promoters within a single construct.

Two or more polynucleotides, one construct. In this expression vector, both the first and at least the second polynucleotides are placed under the control of separate promoters, in a single plasmid construct. This enables the expression of each polynucleotide as a separate entity; however, the tandem would behave in the plant progeny as a single locus.

Two or more polynucleotides, one promoter. The maize streak virus promoter is a bi-functional promoter able to express genes in two directions. Using this promoter, transcription can be initiated on opposite strands in the vector and in opposite directions. Therefore, each polynucleotide can be expressed from a single promoter.

Two or more polynucleotides, two or more constructs. In another approach, two or more separate vector constructs are made, each containing one of the polynucleotides under the direction of different promoters. This approach requires that the plant be doubly transformed.

Cells modified according to the present invention are contemplated at each stage of the invention. This invention further contemplates the introduction of at least one polynucleotide whose enzyme activity is optimal within a temperature range that extends beyond that of the native enzyme and thereby broadens the temperature range in which the enzyme is active in the cell.

Host cells are useful for making, storing, reproducing or manipulating polynucleotide constructs of the invention. Contemplated host cells are eukaryotic cells, such as yeast or plant cells. Prokaryotic host cells containing constructs and/or vectors according to the invention are also contemplated (i.e., *E. coli*).

I.D. Plants and Plant Parts

As used herein, a plant refers to a whole plant, a plant organ (e.g., leaves, stems, roots, etc.), a seed, a plant cell, a propagule, an embryo, and progeny of the same. Plant cells can be differentiated or undifferentiated (e.g., callus, suspension culture cells, protoplasts, leaf cells, root cells, phloem cells, pollen). The present invention may be used for introduction of polynucleotides into any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, *macadamia*, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Crop plants are also of interest, including, for example, maize, sorghum, wheat, sunflower, tomato, crucifers, peppers, potato, cotton, rice, soybean, sugarbeet, sugarcane, tobacco, barley, oilseed rape, etc.

This invention is suitable for any member of the monocot plant family including, but not limited to, maize, rice, barley, oats, wheat, sorghum, rye, sugarcane, pineapple, yams, onion, banana, coconut, and dates.

II. Methods

The present invention provides methods of conferring a trait of interest to a plant by introducing into a plant at least (a) a first heterologous polynucleotide encoding a first polypeptide capable of conferring said trait of interest, and (b) a second heterologous polynucleotide encoding a second polypeptide capable of conferring said trait of interest, wherein said first and second polynucleotides are stably expressed in said plant, and wherein said plant shows said trait of interest over a broader spectrum of a physiological or environmental condition as compared to a plant comprising either said first or second polynucleotide expressed alone and subject to said spectrum of a physiological or environmental condition. In other aspects of the invention, a second heterologous polynucleotide is introduced into a plant that already harbors a first heterologous polynucleotide. Accordingly, a method of conferring a trait of interest can also comprise (a) providing a transgenic plant comprising a first heterologous polynucleotide encoding a first polypeptide capable of conferring said trait of interest, and (b) introducing into said plant at least a second heterologous polynucleotide encoding a second polypeptide capable of conferring said trait of interest, wherein said first and second polynucleotides are stably expressed in said plant, and wherein said plant shows said trait of interest over a broader spectrum of a physiological or environmental condition as compared to a plant comprising either said first or second polynucleotide expressed alone and subject to said spectrum of a physiological or environmental condition. Relevant traits of interest are described herein above, including for example, herbicide resistance and plant yield.

In one such method, at least two polynucleotides encoding polypeptides that confer resistance to an herbicide of interest are introduced into a plant, wherein expression of the at least two polynucleotides increases enzyme activity over a broader spectrum of temperatures than expression of either polynucleotide alone. As discussed elsewhere herein, various polynucleotides can be employed in this method including, but not limited to, EPSP sequences that can confer resistance to glyphosate.

The disclosed methods can also be used to improve plant yield, i.e., the quality and/or quantity of biomass produced by the plant. Biomass is a measurable amount or weight of a plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase.

Plants produced using the disclosed methods can be treated with an effective concentration of an herbicide, where the herbicide application results in enhanced plant yield. An effective concentration is a concentration which allows the increased yield in the plant. Such effective concentrations for herbicides of interest are generally known in the art. The herbicide may be applied either pre- or post emergence in accordance with usual techniques for herbicide application to fields comprising crops which have been rendered resistant to the herbicide.

II.A. Plant Transformation

Methods of the invention involve introducing one or more polynucleotides into a plant by presenting to the plant the polynucleotide in such a manner that the polynucleotide gains access to the interior of a cell of the plant. The methods of the invention do not require that a particular method for introducing a polynucleotide into a plant is used, only that the polynucleotide gains access to the interior of at least one cell of the plant.

Introduction of a polynucleotide into plant cells is accomplished by one of several techniques known in the art, including but not limited to electroporation or chemical transformation (See e.g. Ausubel, ed. (1994) *Current Protocols in Molecular Biology*, John Wiley and Sons, Inc., Indianapolis, Ind. Markers conferring resistance to toxic substances are useful in identifying transformed cells (having taken up and expressed the test polynucleotide sequence) from non-transformed cells (those not containing or not expressing the test polynucleotide sequence). In one aspect of the invention, genes are useful as a marker to assess introduction of DNA into plant cells. Transgenic plants, transformed plants, or stably transformed plants, or cells, tissues or seed of any of the foregoing, refer to plants that have incorporated or integrated exogenous polynucleotides into the plant cell. Stable transformation refers to introduction of a polynucleotide construct a plant such that it integrates into the genome of the plant and is capable of being inherited by progeny thereof.

In general, plant transformation methods involve transferring heterologous DNA into target plant cells (e.g., immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent (i.e., temperature and/or herbicide). The shoots are then transferred to a selective rooting medium for recovering rooted shoot or plantlet. The transgenic plantlet then grow into mature plant and produce fertile seeds (e.g., Hiei et al. (1994) *Plant J.* 6:271-282; Ishida et al. (1996) *Nat. Biotechnol.* 14:745-750). A general description of the techniques and methods for generating transgenic plants are found in Ayres and Park (1994) *CRC Crit. Rev. Plant Sci.* 13:219-239, and Bommineni and Jauhar (1997) *Maydica* 42:107-120. Since the transformed material contains many cells, both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants. Then molecular and biochemical methods can be used for confirming the presence of the integrated nucleotide(s) of interest in the genome of transgenic plant.

Generation of transgenic plants may be performed by one of several methods, including but not limited to introduction of heterologous DNA by *Agrobacterium* into plant cells (Agrobacterium-mediated transformation), bombardment of plant cells with heterologous foreign DNA adhered to particles, and various other non-particle direct-mediated methods (e.g., Hiei et al. (1994) *Plant J.* 6:271-282; Ishida et al. (1996) *Nat. Biotechnol.* 14:745-750; Ayres and Park (1994) *CRC Crit. Rev. Plant Sci.* 13:219-239; Bommineni and Jauhar (1997) *Maydica* 42:107-120) to transfer DNA.

There are three common methods to transform plant cells with *Agrobacterium*. The first method is co-cultivation of *Agrobacterium* with cultured isolated protoplasts. This method requires an established culture system that allows culturing protoplasts and plant regeneration from cultured protoplasts. The second method is transformation of cells or tissues with *Agrobacterium*. This method requires (a) that the plant cells or tissues can be transformed by *Agrobacterium* and (b) that the transformed cells or tissues can be induced to regenerate into whole plants. The third method is transformation of seeds, apices or meristems with *Agrobacterium*. This method requires micropropagation.

The efficiency of transformation by *Agrobacterium* may be enhanced by using a number of methods known in the art. For example, the inclusion of a natural wound response molecule such as acetosyringone (AS) to the *Agrobacterium* culture has been shown to enhance transformation efficiency with *Agrobacterium tumefaciens* (Shahla et al. (1987) *Plant Molec. Biol.* 8:291-298). Alternatively, transformation efficiency may be enhanced by wounding the target tissue to be transformed. Wounding of plant tissue may be achieved, for example, by punching, maceration, bombardment with microprojectiles, etc. See e.g. Bidney et al. (1992) *Plant Molec. Biol.* 18:301-313.

In another aspect of the invention, the plant cells are transfected with vectors via particle bombardment (i.e., with a gene gun). Particle mediated gene transfer methods are known in the art, are commercially available, and include, but are not limited to, the gas driven gene delivery instrument described in McCabe, U.S. Pat. No. 5,584,807, the entire contents of which are herein incorporated by reference. This method involves coating the polynucleotide sequence of interest onto heavy metal particles, and accelerating the coated particles under the pressure of compressed gas for delivery to the target tissue.

Other particle bombardment methods are also available for the introduction of heterologous polynucleotide sequences into plant cells. Generally, these methods involve depositing the polynucleotide sequence of interest upon the surface of small, dense particles of a material such as gold, platinum, or tungsten. The coated particles are themselves then coated onto either a rigid surface, such as a metal plate, or onto a carrier sheet made of a fragile material such as mylar. The coated sheet is then accelerated toward the target biological tissue. The use of the flat sheet generates a uniform spread of accelerated particles that maximizes the number of cells receiving particles under uniform conditions, resulting in the introduction of the polynucleotide sample into the target tissue.

Specific initiation signals may also be used to achieve more efficient translation of sequences encoding the polypeptide of interest. Such signals include the ATG initiation codon and adjacent sequences. In cases where sequences encoding the polypeptide of interest, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers that are appropriate for the particular cell system that is used, such as those described in the literature (Scharf et al. (1994) *Results Probl. Cell Differ.* 20:125).

The cells that have been transformed may be grown into plants in accordance with conventional ways. See e.g. McCormick et al. (1986) *Plant Cell Rep.* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as transgenic seed) having a polynucleotide of the invention, for example, an expression cassette of the invention, stably incorporated into their genome.

Transgenic plants of the invention can be homozygous for the added polynucleotides; i.e., a transgenic plant that contains two added sequences, one sequence at the same locus on each chromosome of a chromosome pair. A homozygous transgenic plant can be obtained by sexually mating (selfing) an independent segregant transgenic plant that contains the added sequences according to the invention, germinating some of the seed produced and analyzing the resulting plants produced for enhanced enzyme activity (i.e., herbicide resistance) and/or increased plant yield relative to a control (native, non-transgenic) or an independent segregant transgenic plant.

It is to be understood that two different transgenic plants can also be mated to produce offspring that contain two independently segregating added, exogenous polynucleotides. Selfing of appropriate progeny can produce plants that are homozygous for all added, exogenous polynucleotides that encode a polypeptide of the present invention. Backcrossing to a parental plant and outcrossing with a non-transgenic plant are also contemplated.

II.B. Evaluation Transformed Plants

Following introduction of DNA into plant cells, the transformation or integration of the polynucleotide into the plant genome is confirmed by various methods such as analysis of polynucleotides, polypeptides and metabolites associated with the integrated sequence.

PCR analysis is a rapid method to screen cells, tissue or shoots for the presence of incorporated gene at the earlier stage before transplanting into the soil (Sambrook and Russell (2001) *Molecular Cloning: A Laboratory Manual*, Cold Spring Harbor Laboratory Press, Cold Spring Harbor, N.Y. PCR is carried out using oligonucleotide primers specific to the nucleotide of interest or *Agrobacterium* vector background, etc.

Introduction of DNA may be confirmed by Southern blot analysis of genomic DNA (Sambrook and Russell (2001) supra). In general, total DNA is extracted from the cell or organism, digested with appropriate restriction enzymes, fractionated in an agarose gel and transferred to a nitrocellulose or nylon membrane. The membrane or blot then is probed with, for example, radiolabeled $^{32}$P-labeled target DNA fragment to confirm the integration of introduced DNA into the plant genome according to standard techniques (Sambrook and Russell (2001) supra).

In Northern analysis, RNA is isolated from specific tissues of the cell or organism, fractionated in a formaldehyde agarose gel, and blotted onto a nylon filter according to standard procedures that are routinely used in the art (Sambrook and Russell (2001) supra). Expression of RNA encoded by the polynucleotide of the present invention is then tested by hybridizing the filter to a radioactive probe derived from the sequence of interest, by methods known in the art (Sambrook and Russell (2001) supra).

Western blot and biochemical assays and the like may be carried out on the transgenic plants to determine the presence of polypeptide encoded by the nucleotide(s) of interest by standard procedures (Sambrook and Russell, 2001,) using antibodies that bind to one or more epitopes present on the herbicide resistance polypeptide.

EXAMPLES

Example 1

EPSP Synthases for Glyphosate Resistance

The DNA coding sequence and the amino acid sequence of the grg8 open reading frame are provided in U.S. Provisional Patent Application No. 60/640,195, filed Dec. 29, 2004, and set forth as SEQ ID NO:1 and SEQ ID NO:2 of this application, respectively.

The DNA coding sequence and the amino acid sequence of the grg23 open reading frame are provided in U.S. Provisional Patent Application No. 60/741,166, filed Dec. 1, 2005, and set forth as SEQ ID NO:3 and SEQ ID NO:4 of this application, respectively.

The DNA coding sequence and amino acid sequence of the grg1 open reading frame are provided in U.S. Provisional patent application Ser. No. 10/739,610, filed Dec. 18, 2003, and set forth as SEQ ID NO:5 and SEQ ID NO:6 of this application, respectively.

The DNA coding sequence and amino acid sequence of the grg20 open reading frame are set forth as SEQ ID NO:7 and SEQ ID NO:8 of this application, respectively. This EPSPS is described in the art as from *Sulfolobus solfataricus* (American Type Culture Collection Accession No. 35092D). U.S. Provisional Application 60/658,320, filed Jan. 12, 2006, describes the discovery of its use as conferring herbicide resistance and teaches domains predictive of such resistance.

Example 2

EPSP Synthase Activity for Temperature Optima Determination

Individual glyphosate-resistant EPSP synthase enzymes were overexpressed in *E. coli* and purified to homogeneity by standard methods. To measure enzyme activity, each enzyme was diluted to an appropriate assay concentration in buffer containing HEPES (50 mM, pH 7) and 50 mM KCl, and then incubated for 15 minutes at 10, 20, 30, 40, 50 or 60° C. Following incubation, each enzyme was heated to 90° C. for 1 minute to denature the enzyme, and then cooled to 4° C. The phosphate generated by each reaction was then added to a second assay containing inosine, purine nucleoside phosphorylase, xanthine oxidase, horseradish peroxidase, and the fluorescent substrate Amplex Red (see U.S. Provisional Patent Application No. 60/741,166, filed Dec. 1, 2005). Following incubation for 15 minutes at room temperature, fluorescent product was quantified using a Gemini XPS spectrofluorometer (Molecular Devices Corporation of Sunnyvale, Calif.). EPSP synthase product formation was plotted as a percentage of the temperature which yielded maximal activity, as shown in FIG. 1.

Example 3

EPSP Synthase Activity for pH Optimum Determination

Figure 2:
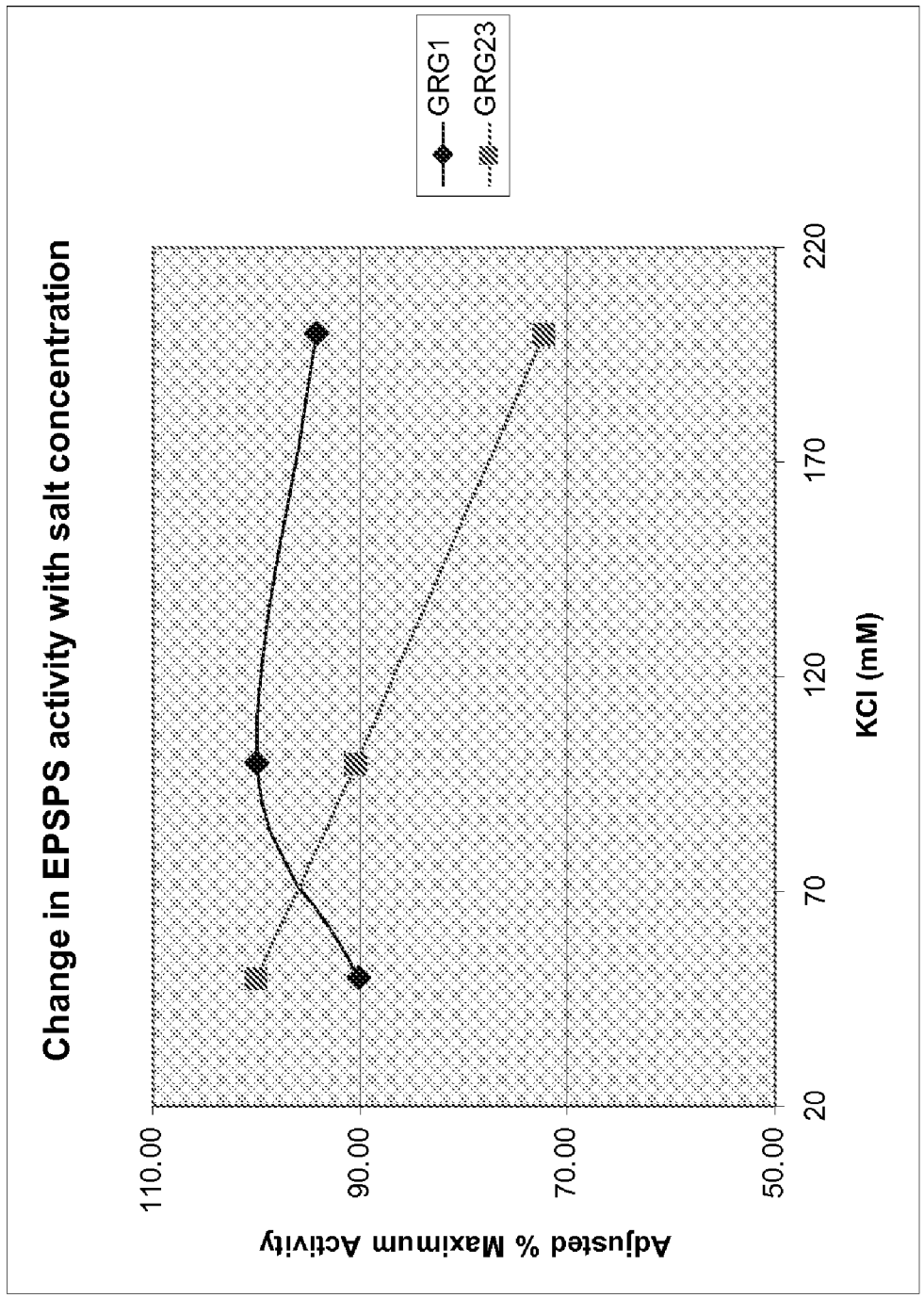
FIG. 2 is a graph depicting the activity of glyphosate resistant EPSP synthase enzymes derived from *Arthrobacter globiformis* (GRG23, SEQ ID NO:4) and Enterobacteriaceae sp. (GRG1, SEQ ID NO:6) as a function of the concentration of salt, expressed in mM.
Figure 3:
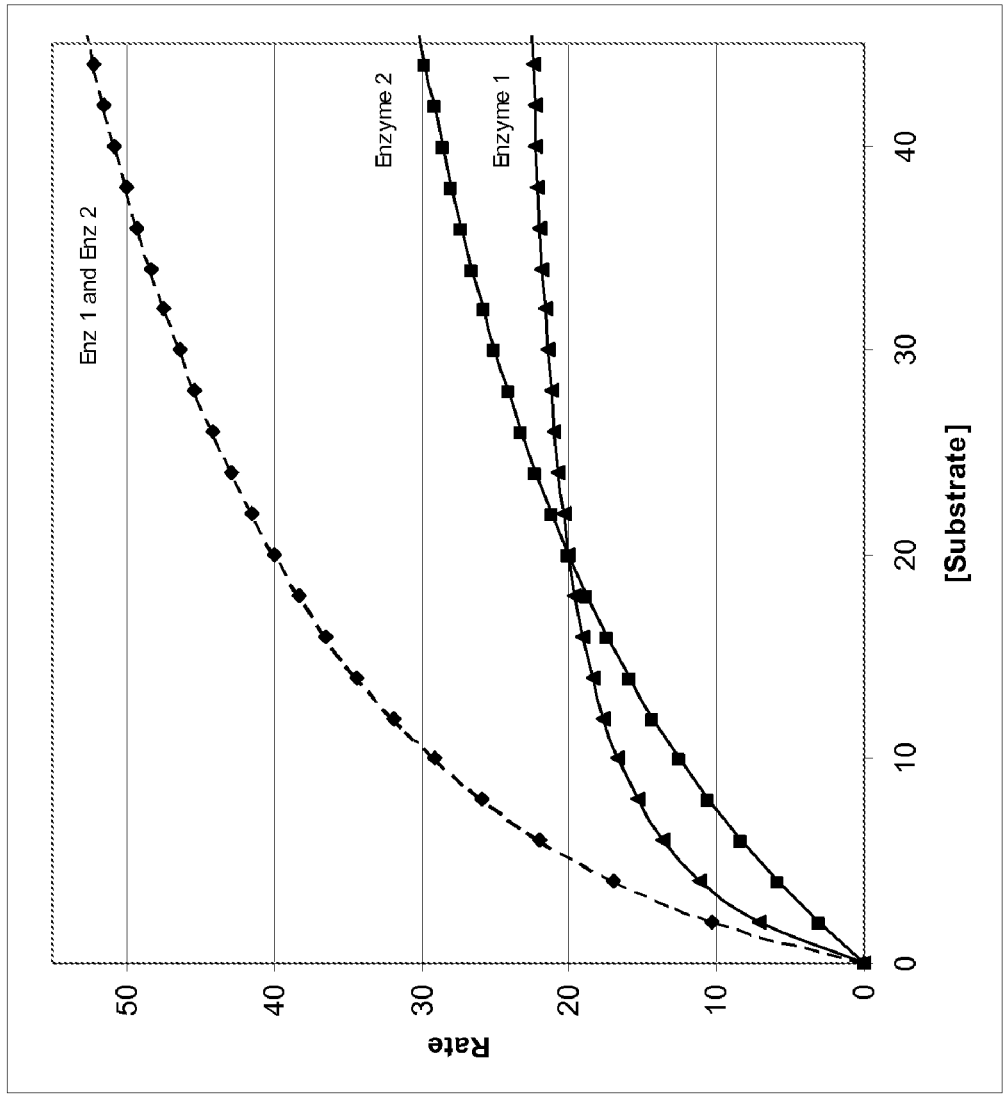
FIG. 3 shows a graph depicting the rate of product formation as a function of substrate concentration for a plant expressing equal amounts of one or both of two enzymes with complementary properties. The 'E1' curve represents the rate of product formation from a plant expressing a said quantity of enzyme 1, where enzyme 1 has a Km for its substrate of 5 µM and a $k_{cat}$ of 25 sec$^{-1}$. The 'E2' curve represents the rate of product formation from a plant expressing a said quantity of E2, where E2 has a Km for its substrate of 30 µM and a $k_{cat}$ of 50 sec$^{-1}$. The 'E1+E2' curve represents the rate of product formation from a plant expressing a said quantity of both E1 and E2.
Figure 4:
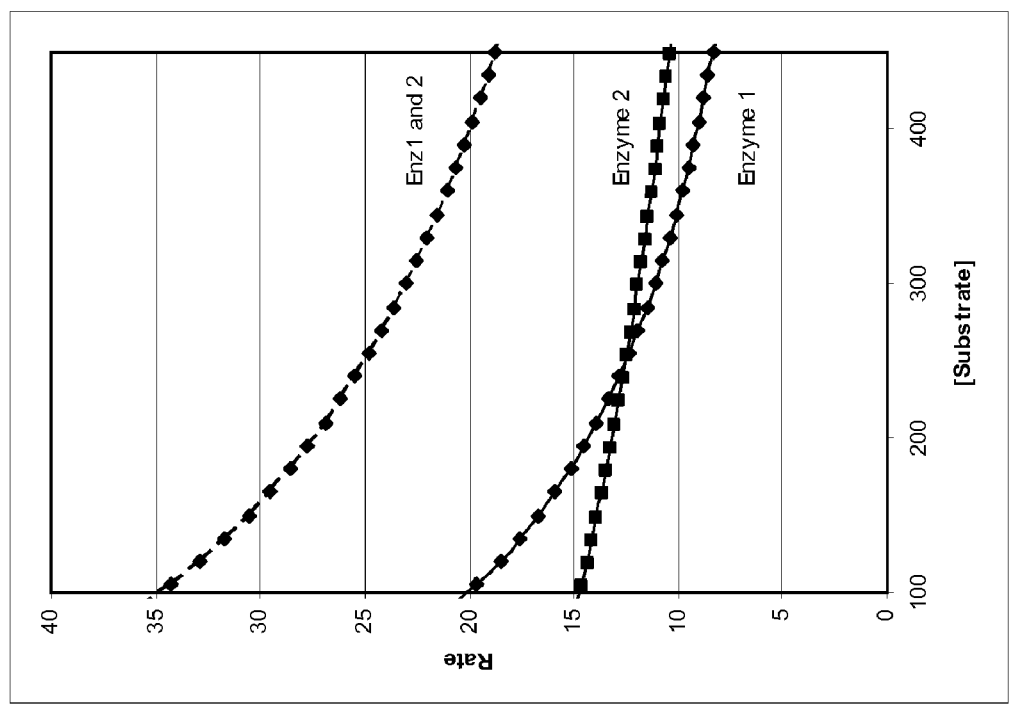
FIG. 4 is a graph depicting the rate of product formation as a function of inhibitor concentration for a plant expressing equal amounts of one or both of two enzymes with complementary properties. The 'E1' curve represents the rate of product formation from a plant expressing a said quantity of enzyme 1, where E1 has a ki of 250 µM, a Km for its substrate of 10 µM, and a $k_{cat}$ of 25 sec$^{-1}$. The 'E2' curve represents the rate of product formation from a plant expressing a said quantity of E2, where E2 has a ki of 50 µM, a Km for its substrate of 10 µM, and a $k_{cat}$ of 50 sec$^{-1}$. The 'E1+E2' curve represents the rate of product formation from a plant expressing a said quantity of both E1 and E2 as a function of the concentration of inhibitor. The concentration of substrate is fixed (in this case, 20 µM).

Individual glyphosate-resistant EPSP synthase enzymes were overexpressed in *E. coli* and purified to homogeneity by standard methods. To measure enzyme activity, each enzyme was diluted to an appropriate assay concentration in buffer containing HEPES (50 mM, pH 7) and 50 mM KCl, and then incubated for 15 minutes with buffers calibrated to pHs ranging from pH 6.0 to pH 8.0. Following incubation, each enzyme was heated to 90.degree. C. for 1 minute to denature the enzyme, and then cooled to 4.degree. C. The phosphate generated by each reaction was then added to a second assay containing inosine, purine nucleoside phosphorylase, xanthine oxidase, horseradish peroxidase, and the fluorescent substrate Amplex Red (see U.S. Provisional Patent Application No. 60/741,166, filed Dec. 1, 2005). Following incubation for 15 minutes at room temperature, fluorescent product was quantified using a Gemini XPS spectrofluorometer (Molecular Devices Corporation of Sunnyvale, Calif.). EPSP synthase product formation was plotted as a percentage of the temperature which yielded maximal activity, as shown in FIG. 2 and in Table 1 below. GRG23 has a pH optimum at or below pH 6, while GRG1 attains maximum activity at pH 7.0. At pH 7.5, GRG1 has a higher percentage activity then GRG23. Thus, a plant cell expressing both GRG1 and GRG23 will have improved activity at a pH range between pH 6.0 and pH 7.5 as compared to a plant cell expressing GRG1 or GRG23 alone.

TABLE 1

| EPSPS | pH | Percent Maximum Activity |
|---|---|---|
| GRG1 | 6.5 | 96.41 |
|  | 7.0 | 100.00 |
|  | 7.5 | 79.11 |
|  | 8.0 | 59.41 |
| GRG23 | 6.5 | 100.00 |
|  | 7.0 | 92.45 |
|  | 7.5 | 71.61 |
|  | 8.0 | 43.81 |

Example 4

EPSP Synthase Activity for Determination of Optimum Salt Concentration

Individual glyphosate-resistant EPSP synthase enzymes were overexpressed in *E. coli* and purified to homogeneity by standard methods. To measure enzyme activity, each enzyme was diluted to an appropriate assay concentration in buffer containing HEPES (50 mM, pH 7) and 50 mM KCl, and then incubated for 15 minutes with buffers supplemented with various amounts of KCL ranging from 50 mM to 200 mM. Following incubation, each enzyme was heated to 90.degree. C. for 1 minute to denature the enzyme, and then cooled to 4.degree. C. The phosphate generated by each reaction was then added to a second assay containing inosine, purine nucleoside phosphorylase, xanthine oxidase, horseradish peroxidase, and the fluorescent substrate Amplex Red (see U.S. Provisional Patent Application No. 60/741,166, filed Dec. 1, 2005). Following incubation for 15 minutes at room temperature, fluorescent product was quantified using a Gemini XPS spectrofluorometer (Molecular Devices Corporation of Sunnyvale, Calif.). EPSP synthase product formation was plotted as a percentage of the KCL concentration which yielded maximal activity, as shown in Table 2 below. GRG23 has maximal activity at a lower KCl concentration than GRG1. Therefore, a plant expressing both GRG1 and GRG2 will have a higher enzyme activity over a broader range of salt concentrations as compared to a plant expressing GRG1 or GRG23 alone.

TABLE 2

| EPSPS | [KCl] | Percent Maximum Activity |
|---|---|---|
| GRG1 | 50 | 94.69 |
|  | 100 | 100 |
|  | 200 | 81.15 |
| GRG23 | 50 | 100 |
|  | 100 | 95.05 |
|  | 200 | 78.18 |

Example 5

Plant Transformation by Particle Bombardment

Maize ears are best collected 8-12 days after pollination. Embryos are isolated from the ears, and those embryos 0.8-1.5 mm in size are used for transformation. Embryos are plated scutellum side-up on a suitable incubation media. DN62A5S media is one such media and is prepared as follows: combine 3.98 g/L N6 salts; 1 mL/L (of 1000× stock) N6 vitamins; 800 mg/L L-asparagine; 100 mg/L myo-inositol; 1.4 g/L L-proline; 100 mg/L casamino acids; 50 g/L sucrose; 1 mL/L (of 1 mg/mL stock) 2,4-D); adjust to pH 5.8 with 1N KOH/1N KCl; add gelrite (Sigma) at a concentration of 3 g/L; after autoclaving and cooling to 50° C., 2 ml/L of a 5 mg/ml stock solution of Silver Nitrate (Phytotechnology Labs) is added and media is poured into plates. Media and salts other than DN62A5S are also suitable and are known in the art. Embryos are incubated overnight at 25° C. in the dark. Embryos may also be incubated for variable times as sufficient to achieve plant transformation.

The resulting explants are transferred to mesh squares (30-40 per plate), transferred onto osmotic media for about 30-45 minutes, then transferred to a beaming plate (see e.g., PCT International Publication No. WO/0138514 and U.S. Pat. No. 5,240,842).

DNA constructs designed to express a first and second EPSP synthase with varying kinetic optima in plant cells are accelerated into plant tissue using an aerosol beam accelerator, using conditions essentially as described in PCT International Publication No. WO 01/38514. After beaming, embryos are incubated for about 30 minutes on osmotic media, and placed onto incubation media overnight at 25° C. in the dark. Care is taken to avoid unduly damaging beamed explants, for example, by incubating embryos for at least 24 hours prior to transfer to recovery media. Embryos are then spread onto recovery period media, for about 5 days, 25° C. in the dark, and then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants. The plants are assayed for improved resistance to glyphosate over a broader range of a physiological or environmental condition (e.g., temperature, pH, concentration of a substrate for said first and second polypeptide, concentration of a cofactor for said first and second polypeptide, concentration of free radicals or free radical donors, concentration of an inhibitor of said first and second polypeptide, or concentration of a catalyst of said first and second polypeptide) than when only a single ESP sequence is expressed. Alternatively, the plants can be assayed for increase yield when compared to expression of only one of the EPSP synthase sequences.

Example 6

Transformation of Plant Cells by Agrobacterium-Mediated Transformation

Ears are collected 8-12 days after pollination. Embryos are isolated from the ears, and those embryos about 0.8-1.5 mm in size are used for transformation. Embryos are plated scutellum side-up on a suitable incubation media, and incubated overnight at 25° C. in the dark. Embryos may also be incubated for variable times as sufficient to achieve plant transformation. Embryos are contacted with an Agrobacterium strain containing the appropriate vectors having two EPSP synthase sequences that are capable of conferring resistance to glyphosate and having varying kinetic optima for Ti plasmid mediated transfer for about 5-10 minutes, and then plated onto co-cultivation media for about 3 days (25° C. in the dark). After co-cultivation, explants are transferred to recovery period media for about five days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art. The resulting shoots are allowed to root on rooting media, and the resulting plants are transferred to nursery pots and propagated as transgenic plants. The plants are assayed for improved resistance to glyphosate over a broader range of a physiological or environmental condition (e.g., temperature, pH, concentration of a substrate for said first and second polypeptide, concentration of a cofactor for said first and second polypeptide, concentration of free radicals or free radical donors, concentration of an inhibitor of said first and second polypeptide, or concentration of a catalyst of said first and second polypeptide) than when only a single ESP sequence is expressed. Alternatively, the plants can be assayed for increase yield when compared to expression of only one of the EPSP synthase sequences.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, certain changes and modifications may be practiced within the scope of the appended claims. Many modifications of the inventions set forth herein will come to mind to one skilled in the art to which these inventions pertain having the benefit of the teachings presented in the foregoing descriptions and the associated drawings. Therefore, it is to be understood that the inventions are not to be limited to the specific examples disclosed and that modifications and other examples are intended to be included within the scope of the appended claims. Although specific terms are employed herein, they are used in a generic and descriptive sense only and not for purposes of limitation.

What is claimed:

1. A plant comprising at least (a) a first heterologous polynucleotide encoding a first EPSP synthase polypeptide capable of conferring increased yield or increased herbicide tolerance, wherein said first heterologous polynucleotide encodes a polypeptide having at least 95% sequence identity to SEQ ID NO:4, and (b) a second heterologous polynucleotide encoding a second EPSP synthase polypeptide capable of conferring said increased yield or increased herbicide tolerance, wherein said first and second polynucleotides are stably expressed in said plant, and wherein said plant shows said increased yield or increased herbicide tolerance over a broader range of a physiological or environmental condition as compared to a plant comprising either said first or second polynucleotide expressed alone and subject to said range of a physiological or environmental condition.

2. The plant of claim 1, wherein said second EPSP polypeptide comprises an amino acid sequence having at least 95% sequence identity to the amino acid sequence of SEQ ID NO: 2, 6, or 8.

3. The plant of claim 2, wherein said first EPSP synthase polypeptide comprises the amino acid sequence of SEQ ID NO: 4 and the second EPSP synthase polypeptide comprises the amino acid sequence of SEQ ID NO:6 or 8.

4. The plant of claim 1, wherein said physiological or environmental condition is temperature.

5. The plant of claim 4, wherein said first EPSP synthase polypeptide has optimal enzyme activity within a temperature range of about 5° C. to about 40° C.

6. The plant of claim 4, wherein said second EPSP synthase polypeptide has optimal enzyme activity at a higher temperature as compared to said first polypeptide and within a temperature range of about 20° C. to about 60° C.

7. The plant of claim 6, wherein said first EPSP synthase polypeptide has optimal enzyme activity within a temperature range of about 10° C. to about 30° C. and said second EPSP synthase polypeptide has optimal enzyme activity at a higher temperature as compared to said first polypeptide and within a temperature range of about 25° C. to about 50° C.

8. The plant of claim 4, wherein expression of said first and said second EPSP synthase polypeptides confers said increased yield or increased herbicide tolerance from about 5° C. to about 60° C.

9. The plant of claim 1, wherein said physiological or environmental condition is pH.

10. The plant of claim 9, wherein said first EPSP synthase polypeptide has optimal enzyme activity within a pH range of about pH 4.0 to about pH 6.5, and wherein said second EPSP synthase polypeptide has optimal enzyme activity at a higher pH as compared to said first EPSP synthase polypeptide and within the range from about pH 6.0 to about pH 8.5.

11. The plant of claim 10, wherein said second EPSP synthase polypeptide comprises an amino acid having at least 95% sequence identity to the amino acid sequence of SEQ ID NO: 6.

12. The plant of claim 1, wherein said physiological or environmental condition is salt concentration.

13. The plant of claim 12, wherein said first EPSP synthase polypeptide has optimal enzyme activity within a salt concentration range of about 50 mM to 150 mM, and wherein said second EPSP synthase polypeptide has optimal enzyme activity at a higher salt concentration as compared to said first polypeptide and within a range from about 100 mM to 200 mM.

14. The plant of claim 12, wherein said second polypeptide comprises an amino acid sequence having at least 95% sequence identity to the amino acid sequence of SEQ ID NO: 6.

15. The plant of claim 1, wherein said physiological or environmental condition is concentration of a substrate or concentration of a cofactor for said first and second polypeptide.

16. The plant of claim 15, wherein said first EPSP synthase polypeptide has (a) an affinity for substrate or cofactor that is at least about 2-fold greater than an affinity for said substrate or cofactor by said second polypeptide, and (b) a catalytic activity that is at least about 2-fold greater than a catalytic activity of said second polypeptide.

17. The plant of claim 16, wherein said first EPSP synthase polypeptide has an affinity for substrate or cofactor that is at least about 5-fold greater than an affinity for said substrate or cofactor by said second polypeptide.

18. The plant of claim 16, wherein said first EPSP synthase polypeptide has an affinity for substrate or cofactor that is at least about 10-fold greater than an affinity for said substrate or cofactor by said second polypeptide.

19. The plant of claim 16, wherein said first EPSP synthase polypeptide has a catalytic activity that is at least about 5-fold greater than a catalytic activity of said second EPSP synthase polypeptide.

20. The plant of claim 16, wherein said first EPSP synthase polypeptide has a catalytic activity that is at least about 10-fold greater than a catalytic activity of said second polypeptide.

21. The plant of claim 16, wherein said first EPSP synthase polypeptide has (a) an affinity for substrate or cofactor that is at least about 10-fold greater than an affinity for said substrate or cofactor by said second polypeptide, and (b) a catalytic activity that is at least about 10-fold greater than a catalytic activity of said second EPSP synthase polypeptide.

22. The plant of claim 1, wherein said first EPSP synthase polypeptide has optimal enzyme activity in cytoplasm, and said second polypeptide has optimal enzyme activity in chloroplasts.

23. The plant of claim 1, wherein said plant is a monocot.

24. The plant of claim 1, wherein said plant is a dicot.

25. A transformed seed of the plant of claim 1.

26. A method of conferring increased yield or increased herbicide tolerance to a plant, said method comprising introducing into said plant at least (a) a first EPSP synthase heterologous polynucleotide encoding a first polypeptide capable of conferring said increased yield or increased herbicide tolerance, wherein said first heterologous polynucleotide encodes a polypeptide having at least 95% sequence identity to SEQ ID NO:4, and (b) a second heterologous polynucleotide encoding a second EPSP synthase polypeptide capable of conferring said increased yield or increased herbicide tolerance, wherein said first and second polynucleotides are stably expressed in said plant, and wherein said plant shows said increased yield or increased herbicide tolerance over a broader spectrum of a physiological or environmental condition as compared to a plant comprising either said first or second polynucleotide expressed alone and subject to said spectrum of a physiological or environmental condition.

27. A method of conferring increased yield or increased herbicide tolerance to a plant, said method comprising (a) providing a transgenic plant comprising a first heterologous polynucleotide encoding a first EPSP synthase polypeptide capable of conferring said increased yield or increased herbicide tolerance, wherein said first heterologous polynucleotide encodes a polypeptide having at least 95% sequence identity to SEQ ID NO:4, and (b) introducing into said plant at least a second heterologous polynucleotide encoding a second EPSP synthase polypeptide capable of conferring said increased yield or increased herbicide tolerance, wherein said first and second polynucleotides are stably expressed in said plant, and wherein said plant shows said increased yield or increased herbicide tolerance over a broader spectrum of a physiological or environmental condition as compared to a plant comprising either said first or second polynucleotide expressed alone and subject to said spectrum of a physiological or environmental condition.

28. A method of increasing plant vigor or yield comprising:
(a) providing a plant according to claim 1; and
(b) treating the plant with an effective amount of said herbicide to thereby increase plant vigor or yield.

* * * * *